(12) United States Patent  
Huhtamaki et al.

(10) Patent No.: US 10,945,706 B2  
(45) Date of Patent: Mar. 16, 2021

(54) HAND HELD ULTRASOUND PROBE

(71) Applicant: Biim Ultrasound AS, Narvik (NO)

(72) Inventors: Jari Huhtamaki, Oulu (FI); Tuomo Liedes, Jaali (FI); Tanar Ulric, Woodinville, WA (US); Craig Bockenstedt, Bothell, WA (US); Blake Little, Fox Island, WA (US); Trygve Burchardt, Howell, MI (US)

(73) Assignee: BIIM ULTRASOUND AS

( * ) Notice: Subject to any disclaimer, the term of this patent is extended or adjusted under 35 U.S.C. 154(b) by 330 days.

(21) Appl. No.: 15/785,091

(22) Filed: Oct. 16, 2017

(65) Prior Publication Data

US 2018/0317883 A1 Nov. 8, 2018

Related U.S. Application Data

(60) Provisional application No. 62/502,323, filed on May 5, 2017.

(51) Int. Cl.  
*A61B 8/00* (2006.01)  
*G10K 11/00* (2006.01)  
(Continued)

(52) U.S. Cl.  
CPC .......... *A61B 8/4455* (2013.01); *A61B 8/4427* (2013.01); *A61B 8/4444* (2013.01); *A61B 8/4461* (2013.01); *A61B 8/4472* (2013.01); *G10K 11/002* (2013.01); *G10K 11/004* (2013.01); *G10K 11/30* (2013.01); *G10K 11/346* (2013.01); *G10K 11/357* (2013.01); *A61B 8/4254* (2013.01); *A61B 8/4281* (2013.01); *A61B 8/44* (2013.01); *A61B 8/4494* (2013.01); *A61B 8/565* (2013.01); *B06B 1/0215* (2013.01)

(58) Field of Classification Search  
CPC .. G10K 11/002; G10K 11/004; G10K 11/357; G10K 11/346; G10K 11/30; B06B 1/0215  
See application file for complete search history.

(56) References Cited

U.S. PATENT DOCUMENTS

| 3,096,444 A | 7/1963 | Seward |
| 3,403,671 A | 10/1968 | Flaherty et al. |

(Continued)

FOREIGN PATENT DOCUMENTS

| EP | 0 110 593 | 6/1984 |
| EP | 0 696 435 | 2/1996 |

(Continued)

OTHER PUBLICATIONS

PCT International Search Report and Written Opinion re Application No. PCT/IB2018/000627; 19 pages.

(Continued)

*Primary Examiner* — Jeffrey G Hoekstra  
*Assistant Examiner* — Sean D Mattson  
(74) *Attorney, Agent, or Firm* — Foley & Lardner LLP

(57) ABSTRACT

A portable ultrasound probe is described having a mechanical transducer, rotating mirror and mirror motor. The transducer can be used for diagnostic imaging and procedural guidance imaging. The probe has a light weight design for easy one handed use, and can use external processors to provide proper image display with accompanying software.

11 Claims, 21 Drawing Sheets

(51) Int. Cl.
  *G10K 11/35*  (2006.01)
  *G10K 11/34*  (2006.01)
  *G10K 11/30*  (2006.01)
  *B06B 1/02*   (2006.01)

(56) References Cited

U.S. PATENT DOCUMENTS

| | | |
|---|---|---|
| 3,406,564 A | 10/1968 | Phillips et al. |
| 3,447,052 A | 5/1969 | Martin et al. |
| 3,482,106 A | 12/1969 | Anderegg, Jr. et al. |
| 3,654,479 A | 4/1972 | Catherin |
| 3,717,857 A | 2/1973 | Evans |
| 3,731,311 A | 5/1973 | Williams |
| 3,768,014 A | 10/1973 | Smith et al. |
| 3,775,617 A | 11/1973 | Dubauskas |
| 3,782,367 A | 1/1974 | Hochberg et al. |
| 3,882,277 A | 5/1975 | DePedro et al. |
| 3,885,552 A | 5/1975 | Kennedy |
| 3,898,984 A | 8/1975 | Mandel et al. |
| 3,909,599 A | 9/1975 | Trott, Jr. et al. |
| 3,927,661 A | 12/1975 | Takemura |
| 3,927,662 A | 12/1975 | Ziedonis |
| 3,972,320 A | 8/1976 | Kalman |
| 4,027,146 A | 5/1977 | Gilmore |
| 4,030,347 A | 6/1977 | Norris et al. |
| 4,034,744 A | 7/1977 | Goldberg |
| 4,048,616 A | 9/1977 | Hart et al. |
| 4,058,001 A | 11/1977 | Waxman |
| 4,081,206 A | 3/1978 | Lee |
| 4,083,366 A | 4/1978 | Gombrich et al. |
| 4,084,582 A | 4/1978 | Nigam |
| 4,095,050 A | 6/1978 | Beachman et al. |
| 4,098,132 A * | 7/1978 | Mikesell ............... G01N 29/221 |
| | | 73/639 |
| 4,100,916 A | 7/1978 | King |
| 4,106,492 A | 8/1978 | Schuette et al. |
| 4,149,420 A | 4/1979 | Hutchison et al. |
| 4,208,602 A * | 6/1980 | Stoller ................. G01N 29/221 |
| | | 310/335 |
| 4,237,729 A | 12/1980 | McLeod et al. |
| 4,240,295 A | 12/1980 | Uranishi |
| 4,241,324 A | 12/1980 | Douglass et al. |
| 4,242,912 A | 1/1981 | Burckhardt |
| 4,245,250 A | 1/1981 | Tiemann |
| 4,246,791 A | 1/1981 | Glenn |
| 4,250,888 A | 2/1981 | Grosskopf |
| 4,252,026 A | 2/1981 | Robinson |
| 4,253,338 A | 3/1981 | Iinuma |
| 4,264,162 A | 4/1981 | Yukio et al. |
| 4,265,121 A | 5/1981 | Cribbs |
| 4,271,706 A | 6/1981 | Ledley |
| 4,271,842 A | 6/1981 | Specht et al. |
| 4,272,991 A | 6/1981 | Cribbs |
| 4,274,421 A * | 6/1981 | Dory ....................... A61B 8/00 |
| | | 367/103 |
| 4,281,664 A | 8/1981 | Duggan |
| 4,287,767 A | 9/1981 | Kretz |
| 4,315,435 A | 2/1982 | Proudian |
| 4,315,514 A | 2/1982 | Drewes et al. |
| 4,316,271 A | 2/1982 | Evert |
| 4,325,381 A | 4/1982 | Glenn |
| 4,326,786 A | 4/1982 | Uchiyama et al. |
| 4,330,874 A | 5/1982 | Sorwick |
| 4,374,525 A | 2/1983 | Baba |
| D269,429 S | 6/1983 | Doyle et al. |
| 4,408,612 A | 10/1983 | Utsugi |
| 4,409,984 A | 10/1983 | Dick |
| 4,413,629 A | 11/1983 | Durley |
| 4,418,698 A | 12/1983 | Dory |
| 4,424,813 A | 1/1984 | Havlice et al. |
| 4,426,886 A | 1/1984 | Finsterwald et al. |
| 4,432,371 A | 2/1984 | McAusland |
| 4,433,691 A | 2/1984 | Bickman |
| 4,446,740 A | 5/1984 | Wilson et al. |
| 4,458,689 A | 7/1984 | Sorenson et al. |
| 4,474,184 A * | 10/1984 | Harui ..................... G10K 11/02 |
| | | 600/459 |
| 4,486,176 A | 12/1984 | Tardieu et al. |
| 4,506,354 A | 3/1985 | Hansen |
| 4,515,017 A | 5/1985 | McConaghy |
| 4,517,985 A | 5/1985 | Teslawski et al. |
| 4,522,213 A | 6/1985 | Wallroth et al. |
| 4,530,362 A | 7/1985 | Hetz |
| 4,531,527 A | 7/1985 | Reinhold et al. |
| 4,535,630 A | 8/1985 | Samodovitz |
| 4,541,434 A | 9/1985 | Okado |
| 4,545,385 A | 10/1985 | Pirschel |
| 4,558,706 A | 12/1985 | Nakada et al. |
| 4,567,883 A | 2/1986 | Langer et al. |
| 4,567,895 A * | 2/1986 | Putzke ................. G10K 11/355 |
| | | 600/445 |
| 4,601,292 A | 7/1986 | Fidel et al. |
| 4,623,219 A | 11/1986 | Trias |
| 4,649,925 A | 3/1987 | Dow et al. |
| 4,732,156 A | 3/1988 | Nakamura |
| 4,757,158 A | 7/1988 | Lentz |
| 4,771,786 A | 9/1988 | Iinuma |
| 4,784,148 A | 11/1988 | Dow |
| 4,794,384 A | 12/1988 | Jackson |
| 4,803,625 A | 2/1989 | Fu et al. |
| 4,807,634 A | 2/1989 | Enjoji et al. |
| 4,814,552 A | 3/1989 | Stefik et al. |
| 4,817,015 A | 3/1989 | Insana et al. |
| 4,819,649 A | 4/1989 | Rogers et al. |
| 4,858,613 A | 8/1989 | Fry et al. |
| 4,862,152 A | 8/1989 | Milner |
| 4,933,229 A | 6/1990 | Insley et al. |
| 4,938,229 A | 7/1990 | Bergelson et al. |
| 5,127,409 A | 7/1992 | Daigle |
| 5,127,410 A | 7/1992 | King et al. |
| 5,142,506 A | 8/1992 | Edwards |
| 5,152,294 A | 10/1992 | Mochizuki et al. |
| 5,159,931 A | 11/1992 | Pini |
| 5,161,535 A | 11/1992 | Short et al. |
| 5,195,519 A | 3/1993 | Angelsen |
| 5,235,510 A | 8/1993 | Yamada et al. |
| 5,245,589 A | 9/1993 | Abel et al. |
| 5,253,530 A | 10/1993 | Letcher |
| 5,291,399 A | 3/1994 | Chaco |
| 5,295,485 A | 3/1994 | Shinomura et al. |
| 5,308,936 A | 5/1994 | Biggs et al. |
| 5,333,612 A | 8/1994 | Wild |
| 5,347,479 A | 9/1994 | Miyazaki |
| 5,367,316 A | 11/1994 | Ikezaki |
| 5,375,602 A | 12/1994 | Lancee et al. |
| 5,383,132 A | 1/1995 | Shinohara et al. |
| 5,392,255 A | 2/1995 | Lebras et al. |
| 5,414,780 A | 5/1995 | Carnahan |
| 5,417,216 A | 5/1995 | Tanaka |
| 5,420,636 A | 5/1995 | Kojima |
| 5,420,891 A | 5/1995 | Akansu |
| 5,456,256 A | 10/1995 | Schneider et al. |
| 5,460,179 A | 10/1995 | Okunuki et al. |
| 5,497,777 A | 3/1996 | Abdel-Malek et al. |
| 5,531,119 A | 7/1996 | Meyers |
| 5,582,173 A | 12/1996 | Li |
| 5,590,658 A | 1/1997 | Chiang et al. |
| 5,603,323 A | 2/1997 | Pflugrath et al. |
| 5,640,960 A | 6/1997 | Jones et al. |
| 5,651,366 A | 7/1997 | Liang et al. |
| 5,655,535 A | 8/1997 | Friemel et al. |
| 5,687,717 A | 11/1997 | Halpern et al. |
| 5,690,110 A | 11/1997 | Tanaka |
| 5,690,114 A | 11/1997 | Chiang et al. |
| 5,715,823 A | 2/1998 | Wood et al. |
| 5,722,412 A | 3/1998 | Pflugrath et al. |
| 5,738,098 A | 4/1998 | Brock-Fisher et al. |
| 5,778,177 A | 7/1998 | Azar |
| 5,817,024 A | 10/1998 | Ogle et al. |
| 5,851,186 A | 12/1998 | Wood et al. |
| 5,853,367 A | 12/1998 | Chalek et al. |
| 5,865,733 A | 2/1999 | Malinouskas et al. |
| 5,867,821 A | 2/1999 | Ballantyne et al. |
| 5,876,342 A | 3/1999 | Chen et al. |

(56) References Cited

U.S. PATENT DOCUMENTS

| | | |
|---|---|---|
| 5,882,300 A | 3/1999 | Malinouskas et al. |
| 5,891,035 A | 4/1999 | Wood et al. |
| 5,893,363 A | 4/1999 | Little et al. |
| 5,899,861 A | 5/1999 | Friemel et al. |
| 5,924,991 A | 7/1999 | Hossack et al. |
| 5,928,151 A | 7/1999 | Hossack et al. |
| 5,944,659 A | 8/1999 | Flach et al. |
| 5,957,846 A | 9/1999 | Chiang et al. |
| 5,964,709 A | 10/1999 | Chiang et al. |
| 5,977,958 A | 11/1999 | Baron et al. |
| 6,006,191 A | 12/1999 | DiRienzo |
| 6,013,032 A | 1/2000 | Savord |
| 6,019,726 A | 2/2000 | Webb |
| 6,063,030 A | 5/2000 | Vara et al. |
| 6,102,860 A | 8/2000 | Mooney |
| 6,106,472 A | 8/2000 | Chiang et al. |
| 6,120,447 A | 9/2000 | Mullen |
| 6,126,602 A | 10/2000 | Savord et al. |
| 6,135,961 A | 10/2000 | Hwang et al. |
| 6,142,946 A | 11/2000 | Hwang et al. |
| 6,196,003 B1 | 3/2001 | Macias et al. |
| 6,241,673 B1 | 6/2001 | Williams |
| 6,246,482 B1 | 6/2001 | Kinrot et al. |
| 6,248,073 B1 | 6/2001 | Gilbert et al. |
| 6,290,648 B1 | 9/2001 | Kamiyama |
| 6,315,724 B1 | 11/2001 | Berman et al. |
| 6,330,057 B1 | 12/2001 | Lederer et al. |
| 6,349,143 B1 | 2/2002 | Hastings et al. |
| 6,375,617 B1 | 4/2002 | Fraser |
| 6,409,669 B1 * | 6/2002 | Hager ............... A61B 8/14 128/916 |
| 6,440,072 B1 | 8/2002 | Schuman et al. |
| 6,459,925 B1 | 10/2002 | Nields et al. |
| 6,468,212 B1 | 10/2002 | Scott et al. |
| 6,516,215 B1 | 2/2003 | Roundhill |
| 6,532,152 B1 | 3/2003 | White et al. |
| 6,535,206 B1 | 3/2003 | Xu |
| 6,540,682 B1 | 4/2003 | Leavitt et al. |
| 6,554,771 B1 | 4/2003 | Buil et al. |
| 6,569,101 B2 | 5/2003 | Quistgaard et al. |
| 6,622,562 B2 | 9/2003 | Angelsen et al. |
| 6,638,229 B2 | 10/2003 | Reyes et al. |
| 6,669,633 B2 | 12/2003 | Brodsky et al. |
| 6,679,849 B2 | 1/2004 | Miller et al. |
| 6,699,191 B2 | 3/2004 | Brock-Fisher |
| 6,709,397 B2 | 3/2004 | Taylor |
| 6,712,765 B2 | 3/2004 | Glenn |
| 6,780,154 B2 | 8/2004 | Hunt et al. |
| 6,891,920 B1 | 5/2005 | Minyard et al. |
| 6,962,566 B2 | 11/2005 | Quistgaard et al. |
| 6,980,419 B2 | 12/2005 | Smith et al. |
| 7,129,963 B2 | 10/2006 | Bohnisch et al. |
| 7,141,020 B2 | 11/2006 | Poland et al. |
| 7,484,412 B2 | 2/2009 | Hart et al. |
| 7,597,664 B2 | 10/2009 | Jones et al. |
| 7,597,665 B2 | 10/2009 | Wilk et al. |
| 7,634,318 B2 | 12/2009 | Tran et al. |
| 7,691,060 B2 | 4/2010 | Angelsen et al. |
| 7,819,807 B2 | 10/2010 | Barnes et al. |
| 8,052,606 B2 | 11/2011 | Barnes et al. |
| 8,096,949 B2 | 1/2012 | Chen et al. |
| 8,128,568 B2 | 3/2012 | Wang et al. |
| 8,221,324 B2 | 7/2012 | Pedersen et al. |
| 8,301,232 B2 | 10/2012 | Albert et al. |
| 8,328,725 B2 | 12/2012 | Anthony et al. |
| 8,372,102 B2 | 2/2013 | Stulen et al. |
| 8,461,978 B2 | 6/2013 | Garner et al. |
| 8,465,433 B2 | 6/2013 | Zwirn |
| 8,517,946 B2 | 8/2013 | Kim |
| 8,684,933 B2 | 4/2014 | Hao et al. |
| 8,690,783 B2 | 4/2014 | Sinelnikov |
| 8,926,533 B2 | 1/2015 | Bockenstedt et al. |
| 9,199,096 B2 | 12/2015 | Lewis |
| 9,254,117 B2 | 2/2016 | Fukushima et al. |
| 9,320,492 B2 | 4/2016 | Havel et al. |
| 9,351,705 B2 | 5/2016 | Wang et al. |
| 9,456,802 B2 | 10/2016 | Zhou et al. |
| 9,629,528 B2 | 4/2017 | Woods et al. |
| 2001/0034484 A1 | 10/2001 | Nakamura et al. |
| 2001/0044588 A1 | 11/2001 | Mault |
| 2002/0014420 A1 | 2/2002 | Schultz et al. |
| 2002/0016545 A1 | 2/2002 | Quistgaard et al. |
| 2002/0035326 A1 | 3/2002 | Kamiyama |
| 2002/0068870 A1 | 6/2002 | Alam et al. |
| 2002/0139193 A1 | 10/2002 | Angelsen et al. |
| 2003/0018269 A1 | 1/2003 | Angelsen et al. |
| 2003/0139671 A1 | 7/2003 | Walston et al. |
| 2003/0163046 A1 | 8/2003 | Nohara et al. |
| 2004/0106869 A1 | 6/2004 | Tepper |
| 2004/0230214 A1 | 11/2004 | Donofrio et al. |
| 2004/0254460 A1 | 12/2004 | Burcher et al. |
| 2005/0018540 A1 | 1/2005 | Gilbert et al. |
| 2005/0075570 A1 | 4/2005 | Shinomura et al. |
| 2005/0215892 A1 | 9/2005 | Emery et al. |
| 2005/0228281 A1 | 10/2005 | Nefos |
| 2005/0251035 A1 | 11/2005 | Wong et al. |
| 2006/0020206 A1 | 1/2006 | Serra et al. |
| 2006/0058652 A1 | 3/2006 | Little |
| 2006/0100530 A1 | 5/2006 | Kliot et al. |
| 2006/0116578 A1 | 6/2006 | Grunwald et al. |
| 2007/0066894 A1 | 3/2007 | Bartol et al. |
| 2007/0159549 A1 | 7/2007 | Matsumoto |
| 2007/0176895 A1 | 8/2007 | Miyasaka et al. |
| 2007/0266548 A1 | 11/2007 | Fattinger |
| 2007/0271528 A1 | 11/2007 | Park et al. |
| 2007/0276250 A1 | 11/2007 | Donaldson |
| 2007/0276292 A1 | 11/2007 | Hansma et al. |
| 2008/0119731 A1 | 5/2008 | Becerra et al. |
| 2008/0208047 A1 | 8/2008 | Delso |
| 2008/0208061 A1 | 8/2008 | Halmann |
| 2008/0312536 A1 * | 12/2008 | Dala-Krishna .......... A61B 8/12 600/459 |
| 2009/0005680 A1 | 1/2009 | Jones et al. |
| 2009/0012396 A1 | 1/2009 | Jones et al. |
| 2009/0043195 A1 | 2/2009 | Poland |
| 2009/0076385 A1 | 3/2009 | Jackson et al. |
| 2009/0149752 A1 | 6/2009 | Osaka et al. |
| 2009/0182228 A1 | 7/2009 | Pierce |
| 2009/0247874 A1 | 10/2009 | Kim |
| 2009/0306509 A1 | 12/2009 | Pedersen et al. |
| 2009/0306515 A1 | 12/2009 | Matsumura et al. |
| 2010/0094132 A1 | 4/2010 | Hansen et al. |
| 2010/0160784 A1 | 6/2010 | Poland et al. |
| 2010/0160785 A1 | 6/2010 | Poland et al. |
| 2010/0160786 A1 | 6/2010 | Nordgren et al. |
| 2010/0168576 A1 * | 7/2010 | Poland .................... A61B 8/00 600/443 |
| 2010/0204694 A1 | 8/2010 | Mehta et al. |
| 2010/0228130 A1 | 9/2010 | Chiang et al. |
| 2010/0249604 A1 | 9/2010 | Hastings et al. |
| 2010/0256502 A1 | 10/2010 | Buckley et al. |
| 2010/0298711 A1 | 11/2010 | Pedersen et al. |
| 2011/0071401 A1 | 3/2011 | Hastings et al. |
| 2011/0118562 A1 | 5/2011 | Smith et al. |
| 2011/0152690 A1 | 6/2011 | Anthony et al. |
| 2011/0172541 A1 | 7/2011 | Anthony et al. |
| 2011/0218436 A1 | 9/2011 | Dewey et al. |
| 2011/0319760 A1 | 12/2011 | Cerofolini |
| 2012/0029393 A1 | 2/2012 | Lee |
| 2012/0101388 A1 | 4/2012 | Tripathi |
| 2012/0101389 A1 | 4/2012 | Tanabe |
| 2012/0130241 A1 | 5/2012 | Wang et al. |
| 2012/0172722 A1 | 7/2012 | Chinowsky et al. |
| 2012/0179037 A1 * | 7/2012 | Halmann ............. A61B 8/4427 600/443 |
| 2012/0296210 A1 | 11/2012 | Pelissier et al. |
| 2012/0323124 A1 * | 12/2012 | Corbett, III .......... A61B 5/6826 600/459 |
| 2013/0172748 A1 | 7/2013 | Kim |
| 2013/0245449 A1 | 9/2013 | Barnes et al. |
| 2013/0253323 A1 | 9/2013 | Kim |
| 2013/0317365 A1 | 11/2013 | Anthony et al. |
| 2013/0321286 A1 | 12/2013 | Petruzzelli et al. |
| 2013/0331694 A1 | 12/2013 | Barnes et al. |

(56) References Cited

U.S. PATENT DOCUMENTS

| | | | |
|---|---|---|---|
| 2014/0031694 A1 | 1/2014 | Solek | |
| 2014/0046185 A1 | 2/2014 | Mo et al. | |
| 2014/0088428 A1 | 3/2014 | Yang et al. | |
| 2014/0240482 A1* | 8/2014 | Ikeda | A61B 8/5207 348/77 |
| 2015/0297182 A1 | 10/2015 | Peng et al. | |
| 2015/0321026 A1 | 11/2015 | Branson et al. | |
| 2016/0151045 A1 | 6/2016 | Pelissier et al. | |
| 2016/0302759 A1 | 10/2016 | Shi et al. | |
| 2017/0153207 A1 | 6/2017 | Burchardt | |

FOREIGN PATENT DOCUMENTS

| | | |
|---|---|---|
| EP | 0749722 | 4/1996 |
| FR | 2579094 | 9/1986 |
| JP | 10-216131 | 8/1998 |
| JP | 10-277038 | 10/1998 |
| JP | 2003-275206 | 9/2003 |
| WO | WO-2010/140126 A2 | 12/2010 |
| WO | WO-2016/024212 | 2/2016 |
| WO | WO16024212 | 2/2016 |
| WO | WO17029598 | 2/2017 |
| WO | WO17029599 | 2/2017 |

OTHER PUBLICATIONS

International Search Report re Application No. PCT/IB2016/054876.

* cited by examiner

HAND HELD ULTRASOUND PROBE

CROSS-REFERENCE TO RELATED PATENT APPLICATIONS

This application claims the benefit of and priority to U.S. Provisional Patent Application No. 62/502,323, filed May 5, 2017, the entire disclosure of which is incorporated by reference herein.

FIELD

The present disclosure is related to the field of hand held ultrasound probes for diagnostic imaging.

BACKGROUND

Ultrasound examinations are an effective procedure to image and assess anatomy or diagnose diseases. The technique has been used for decades around the world. The high cost of devices and the complexity of ultrasound equipment has been a barrier for entry for many qualified clinicians. The result is not all patients who could benefit from ultrasound medical technology have been able to get access to such technology.

SUMMARY

Described herein are various embodiments for a hand held ultrasound probe, a medical ultrasound system, and methods of using the probe and system.

According to one embodiment, there is a hand held ultrasound transducer probe housing that includes a first chamber and a second chamber. The first chamber contains an electronics package for driving an ultrasound transducer and a power supply. The second chamber can be a liquid tight chamber containing an ultrasound transducer, an acoustic mirror, a drive motor for moving the acoustic mirror, an acoustic lens and a flexible membrane to partition the second chamber into a first section and a second section. The flexible membrane serves as a pressure relief for the first section when it is filled with fluid. The second section serves as a buffer space for the flexible membrane to expand into.

According to another embodiment, an ultrasound device includes a chamber containing an ultrasound transducer having a primary axis of transmission and a lens, where the chamber is adapted to be liquid filled. The ultrasound device also includes an anechoic surface positioned outside the primary axis of transmission.

According to another embodiment, the ultrasound probe can have a sensor in a fixed position and lined up so the sensor is within a circumference area defined by the rotating mirror, and a reflector on the rotating mirror and positioned to be detected by the sensor, such that as the rotating mirror moves, the reflector is detected each time it passes over the sensor.

According to another embodiment, a method of minimizing ultrasound image data includes performing a first bit channel reduction on a data set, reducing a percent data rate on a data set, and altering a sample frequency (Fs MHz) based on a variable produced by a decimation reduction of a sample bit (Fs/D MHz), wherein an image data set is reduced in bit volume by at least eighty percent 80%.

According to another embodiment, a method of enhancing ultrasound image data includes receiving a first and a second reduced image data set, creating an intermediate image data set by averaging the first and second image, interleaving the first and second image data sets with the intermediate image data, adjusting all image data sets for a display, and exporting the image data sets to the display.

Another embodiment relates to a method that includes receiving, by an ultrasound probe, software version data from a user computing device. The user computing device comprises a display configured to display images from the ultrasound probe. The method includes determining, by the ultrasound probe, based upon comparison of data on the ultrasound probe with the software version data from the user computing device that an upgrade is available to the ultrasound probe. The method further includes receiving, by the ultrasound probe, a software upgrade data into a memory module of the ultrasound probe, where the software upgrade data comprises data for upgrading at least one portion of the ultrasound probe. The method further includes upgrading, by the ultrasound probe, the at least one portion of the ultrasound probe from the software upgrade data.

Another embodiment relates to a method that includes receiving, by a user computing device, software upgrade data for upgrading software of an ultrasound probe, where the user computing device comprises a display configured to display images from the ultrasound probe. The method also includes establishing communication, by the user computing device, with the ultrasound probe; receiving, by the user computing device, an indication from the ultrasound probe for upgrading the ultrasound probe; downloading, by the user computing device, the software upgrade data onto the ultrasound probe; receiving, by the user computing device, confirmation that the software upgrade data is successfully downloaded onto the ultrasound probe; and issuing, by the user computing device, a rebooting command for causing a reboot of the ultrasound probe.

According to another embodiment, a system includes an ultrasound probe comprising a probe memory module and probe processing unit. The system also includes a user computing device configured to be operatively associated with the ultrasound probe comprising a display configured to display images obtained by the ultrasound probe, the user computing device further comprising a device memory module and a device processing unit. The probe processing unit is configured to: access an upgrade module on the device memory module of the user computing device; determine based upon comparison of data on the ultrasound probe with software version data from the upgrade module that an upgrade is available to the ultrasound probe; receive software upgrade data from the upgrade module into the probe memory module of the ultrasound probe, wherein the software upgrade data comprises data for upgrading at least one portion of the ultrasound probe; and upgrade the at least one portion of the ultrasound probe from the software upgrade data.

The foregoing summary is illustrative only and is not intended to be in any way limiting. In addition to the illustrative aspects, embodiments, and features described above, further aspects, embodiments, and features will become apparent by reference to the following drawings and the detailed description.

DETAILED DESCRIPTION

Figure 1A:
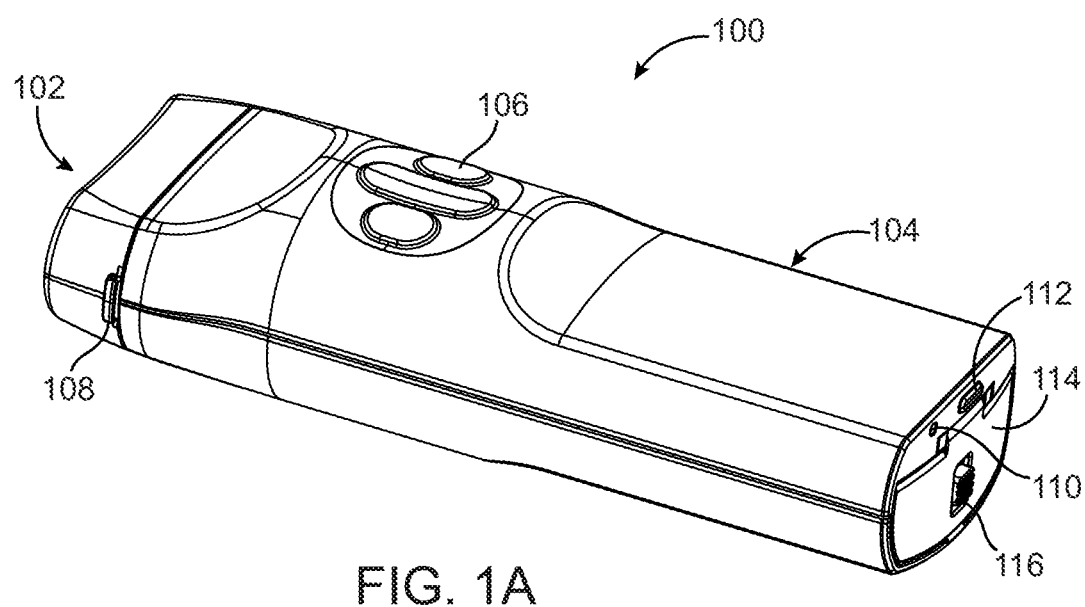
FIGS. 1A-1B illustrate an exterior of an ultrasound probe according to an embodiment.

In the description that follows, certain abbreviations and acronyms are used. Definitions for some of these terms are provided here in Table 1.

TABLE 1

| Term/Acronym | Definition |
| --- | --- |
| ADC | Analog to Digital Converter |
| DAC | Digital to Analog Converter |
| QBP | Quadrature Bandpass |
| RF | Radio Frequency - Before BaseBand |
| TGC | Time Gain Compensation - Gain change with depth or time |
| TX | Transmit |
| RX | Receive |

Described herein are various embodiments for a handheld ultrasound probe. The probe can work in conjunction with an electronic device that has some processing capability and a display. Methods of communicating with the electronic device and the handheld ultrasound prove are also described.

In various embodiments, the ultrasound probe described herein may be useful to clinicians for performing ultrasound imaging scans. Medical ultrasound can be useful for guided vascular access such as for Central Venous Catheters, Peripherally inserted central catheter, peripherally inserted venous catheter, peripheral venous cannulation and arterial line placement. Ultrasound imaging can provide image guidance for airway access in endotracheal tube placement, assessment and/or confirmation of pneumothorax (sliding lung sign). In addition, ultrasound imaging can assist in various physiotherapy and musculoskeletal procedures such as; guiding articular and periarticular aspiration or injection, assess articular pain, swelling or mechanical symptoms, inflammatory arthritis and new or ongoing symptoms, shoulder pain or mechanical symptoms and regional neuropathic pain. Ultrasound imaging can also help assessment of carotid arteries (stroke), guided vascular access, and help determine indications of abscesses or cysts. Ultrasound imaging is useful in pregnancy scans to assess a baby's health, breast examination for tumors, and can be used as a pre-screening modality to determine if additional testing or imaging by other modalities is required.

In some embodiments, there can be an ultrasound probe (or scan head, or simply probe) that may be held and used with one hand. The probe body may be dimensioned to fit in an average adult hand. In addition to being dimensioned for one handed usage, the probe may have ergonomic features to assist in one handed operation. In some embodiments the exterior dimensions of the probe may be about 175 mm (millimeters) long, and about 50 mm high and about 70 mm wide (175×50×70). In some embodiments the probe may be about 160 mm long, by about 40 mm high and 60 mm wide (160×40×60). In some embodiments the probe may be about 150 mm long, about 55 mm wide and about 40 mm wide. In some embodiments the probe may be about 300 g (grams). In still other embodiments the probe may be about 250 g. In still other embodiments the probe may be about 225 g. As used herein the term "about" means roughly the measurement indicated with a margin of error of +/−15%. Similarly the use of the term "substantially" also refers to a variance of +/−15%. The probe body may be made from plastic, organic polymer materials, metal, metal alloy materials, or any combination of these materials. In some embodiments the probe body may use specific materials as detailed herein to provide a specific functionality or feature. In some embodiments, there may be user activated controls in the form of buttons or switches on at least one surface of the probe. In some embodiments multiple control features may be grouped together on at least once surface of the probe. In some embodiments the control features may be grouped together for easier selection of the various controls. In some other embodiments, the control features may be displaced so activation of one or more of the controls would require additional effort by the user so as to not accidentally activate one or more of the controls which are more remotely placed. Some example controls may include; an on/off switch, battery status query, freeze/unfreeze, image save, depth adjustment, shut-down/cleaning/sterilize mode, WiFi status query, device pairing query, test cycle, or other feature.

In some embodiments, the probe can have a front face where an acoustic lens forms part of the probe body. In some embodiments the probe body may have placement for a shield or cap to cover the acoustic lens when the probe is not in use.

The probe may have a casing or housing, divided into two chambers. In an embodiment, the first chamber may contain an electronics package and a power supply. This can be referred to as the electronics or dry chamber. In an embodiment, the second chamber may contain an ultrasound transducer, an acoustic mirror (mirror), and a motor for moving the acoustic mirror. The second chamber may be referred to as the acoustic chamber. The second chamber may also have an acoustic lens (lens) allowing ultrasound energy to pass in and out of the chamber. In some embodiments the second chamber may have a membrane that divides the second chamber into a first partition and a second partition. In some embodiments, the second chamber may have a first fill port (port) capable of receiving a fluid. In some embodiments, the second chamber may have a second fill port or exhaust port. In some embodiments, addition fill or exhaust ports may be provided. In an aspect, the first port may be in close proximity to the second port. In some embodiments the first port and the second port may be in close proximity. In some embodiments the first and second port may be on substantially opposite sides of the chamber. The fill ports may be self-sealing, use a seal valve or plug or cap.

In some embodiments, the first partition contains the transducer, mirror and motor, and has the lens as part of the chamber wall. In some embodiments, there may be an anechoic surface around the mirror, or other interior surfaces of the first partition. In some embodiments the distance from the transducer to the mirror and the distance from the mirror to the lens form a ratio that can be used to improve image quality. The distances also define the axis of the principle transmission of ultrasound energy. In an aspect, the membrane provides a liquid barrier between the first partition and the second partition, so that the first partition may be filled with an ultrasound transmission fluid. The second partition may be filled with air, or easily compressible material. When the first partition is filled with fluid, the membrane can accommodate the expansion of the fluid to maintain a relatively steady state of fluid pressure in the first partition.

In some embodiments, the fluid may be water. In some embodiments the fluid may be mineral oil. In the various embodiments, when the ultrasound transducer is in use, the fluid may experience an increase in thermal energy. This may cause the fluid to expand. The membrane may provide pressure release for the expanding fluid while maintaining coupling on the transducer and the first partition, so there is no degradation or significant change in ultrasound performance.

In some embodiments, the probe has a second chamber containing a power supply and electronic circuitry for controlling and operating the probe. The power supply may be a removable battery. The electronics may be one or more printed circuit board(s) able to fit within the second chamber. The PCB has sufficient components on board to provide all necessary and any desired optional features for the probe. In various embodiments the probe relies on an FPGA for general processing, with a dedicated beamformer for controlling the transducer, and a WiFi chip for wireless connection to a tablet.

The ultrasound scan head can use two software suites, one can be resident on the probe and the other can be resident on the computing device. The two software suites may work in conjunction with each other to generate ultrasound images.

In an embodiment, there may be a first software suite residing on the probe. The software on the probe provides the control over the electronics to produce ultrasound scans, generate images, communicate with external devices, and regulate or monitor all the electrical features of the probe. In an aspect of the software operation, there can be a method for reducing the amount of image data from the transducer to the WiFi device so that amount of data transferred from the probe to a tablet is greatly reduced, without significantly increasing latency of image presentation.

In some embodiments, the probe may communicate with a wireless portable computer device, such as a tablet computer or laptop computer. In some embodiments, the electronics control platform may be a dedicated portable computer device specially designed for use with the probe. In some embodiments, the portable computing device may be a commercially available platform such as a desktop computer, laptop computer, or tablet computer. In various embodiments the tablet device can operate an application program (App) to receive compressed image data from the probe, and convert it into presentable visual ultrasound images for a user. In some embodiments, each new frame of ultrasound image video received from the probe may be processed with a temporal compounding step, speckle reduction and speckle raw image opacity, then each frame is converted into a double frame by a compounding method. Image sharpness is provided and then the received draw frame is converted for the visual display.

Figure 1B:
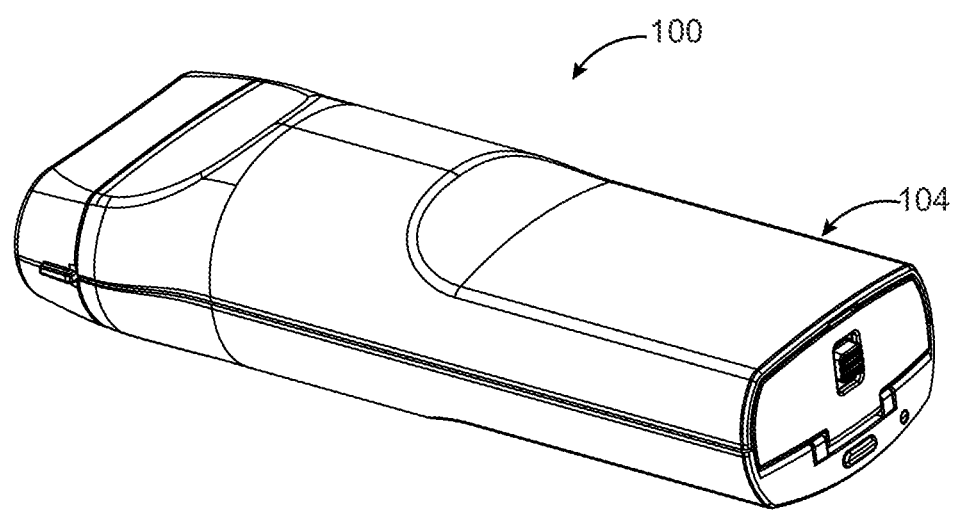

Described herein are various embodiments of a handheld ultrasound probe and accompanying methods of use. In an embodiment, there can be a handheld ultrasound probe 100 with a handle 104 and a front end 102 (FIGS. 1A-B). The probe may be held like a flash light, with one or more user activated controls 106 placed for easy use. The front end 102 can be an acoustic lens and can be the portion of the probe that may be placed on a patient body during an ultrasound scan. The probe may have needle guide 108 on one or both sides, the needle guides may be parallel to the long axis. An LED indicator 110 may have multiple color states for on/in use/trouble and/or low battery. A power button 112 is positioned on the back end, where there is a battery door 114 and a battery door latch 116.

Figure 2:
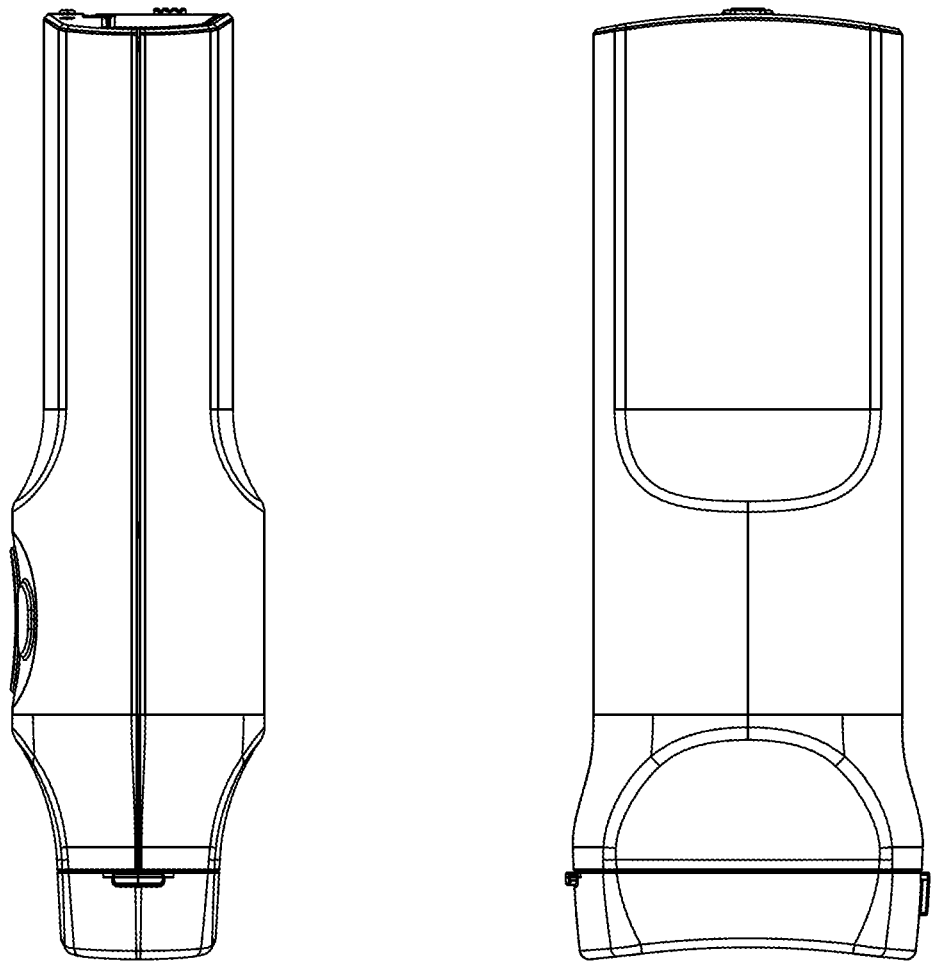
FIG. 2 illustrates a side and bottom view of an ultrasound probe according to an embodiment.
Figure 3A:
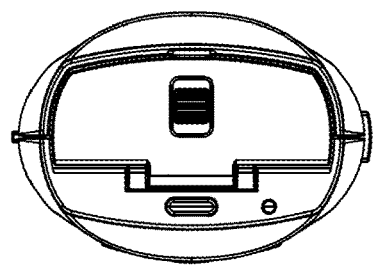
FIGS. 3A-D illustrate various views of an ultrasound probe according to an embodiment.
Figure 3B:
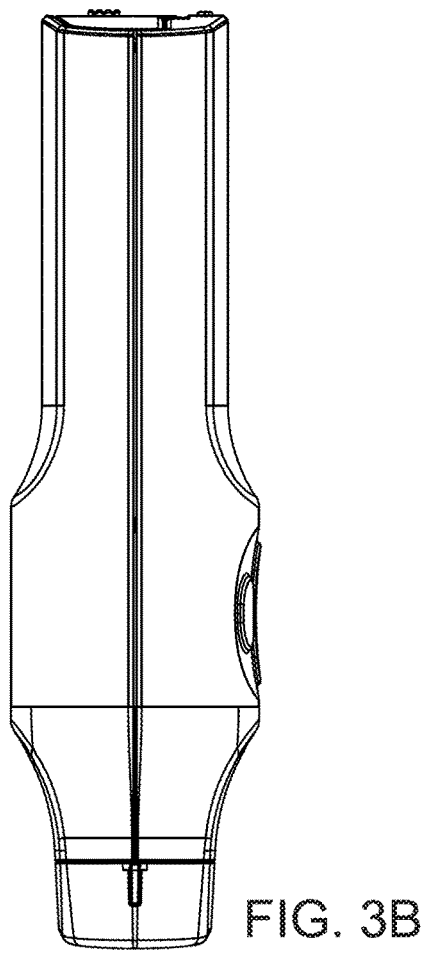
Figure 3C:
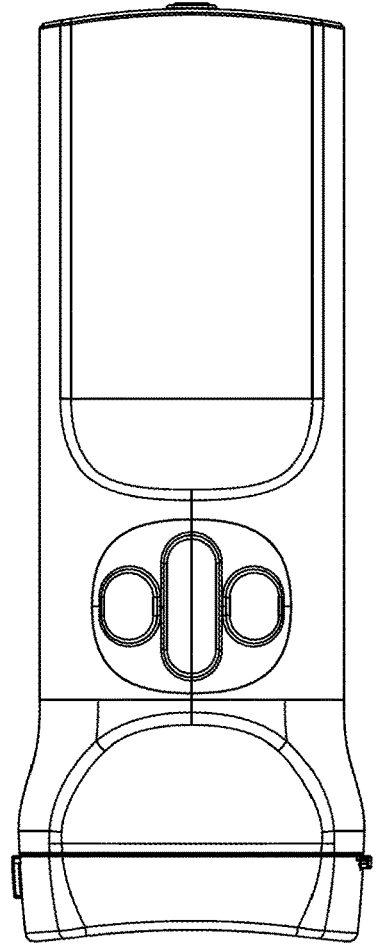
Figure 3D:
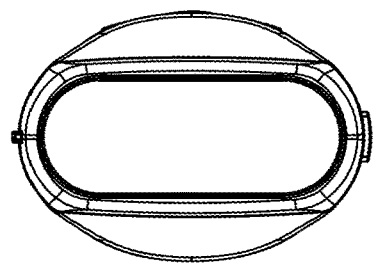
Figure 4:
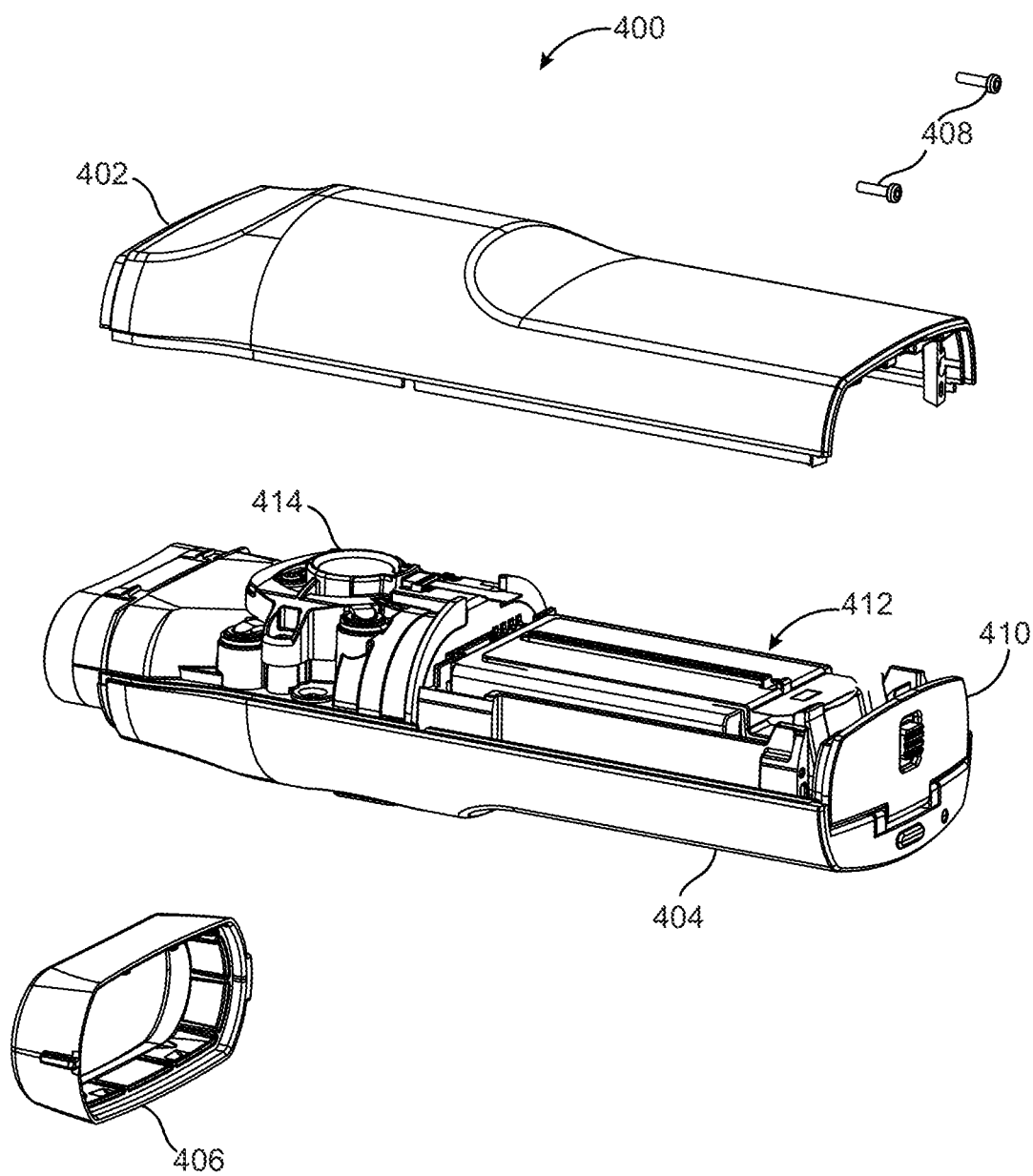
FIG. 4 illustrates a partial interior view of an ultrasound probe according to an embodiment.

In some embodiments, the probe may have a simple ergonomic design (FIG. 2). In other embodiments the design may be elegant and ornamental (FIGS. 3A-D). In an embodiment, the probe 400 can be seen in a partial assembly drawing showing the bottom 402 portion of the body, the top 404 portion of the body, a back plate 410, a lens adapter 406, an electronic package 412 and an acoustic chamber 414. A pair of fasteners 408 can be used to assemble the bottom 402 to the top 404 by securing the top and bottom together through the back plate 410.

Figure 5:
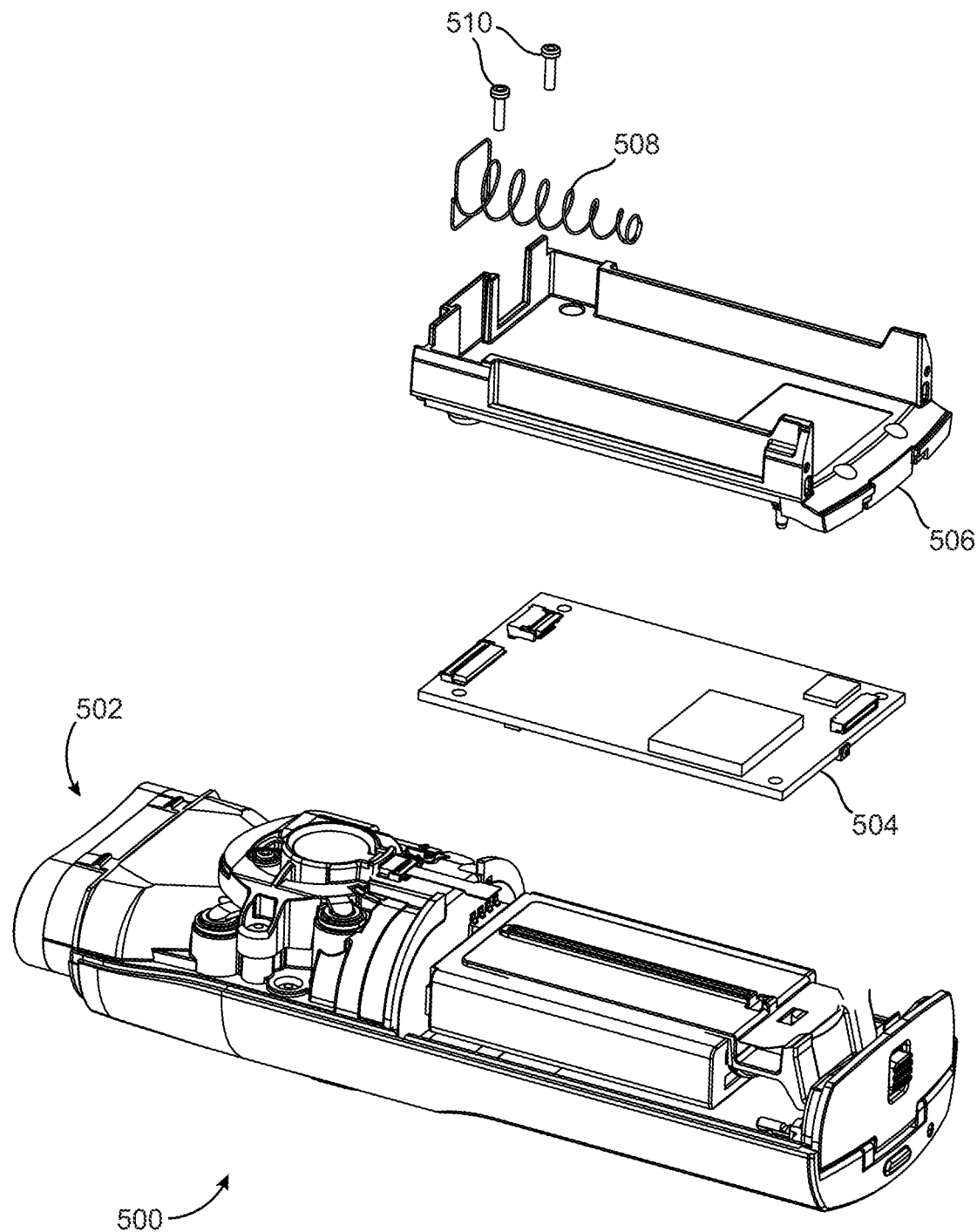
FIG. 5 illustrates a partial exploded view of the electronics chamber of the ultrasound probe according to an embodiment.

In an embodiment, the probe 500 can be seen with all elements in place without the back cover (FIG. 5). A printed circuit board (PCB) 504 can rest under a battery housing 506. The battery housing can have a spring 508 to provide frictional engagement of the battery into the holder/probe. The battery holder and/or PCB may be held in place by a set of fasteners 510.

Figure 6:
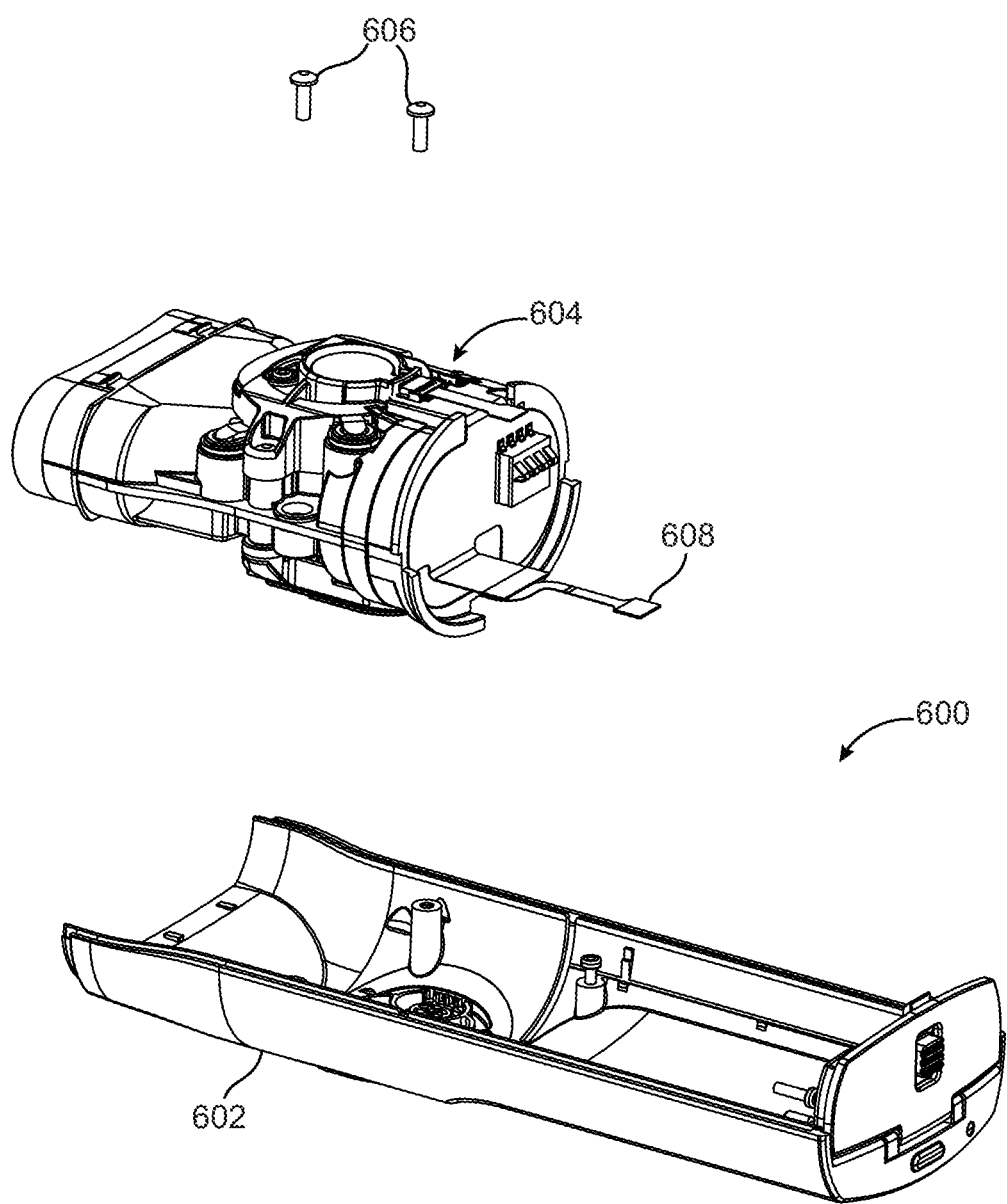
FIG. 6 illustrates the placement of the acoustic chamber in the ultrasound probe according to an embodiment.

In another embodiment, the probe 600 has a top section 602 and an acoustic chamber 604 (FIG. 6). There may be a flex connection 608 for providing electrical communication from the electrical package to the components inside the acoustic chamber. A pair of fasteners 606 are used to hold the acoustic chamber to the top portion 602.

Figure 7A:
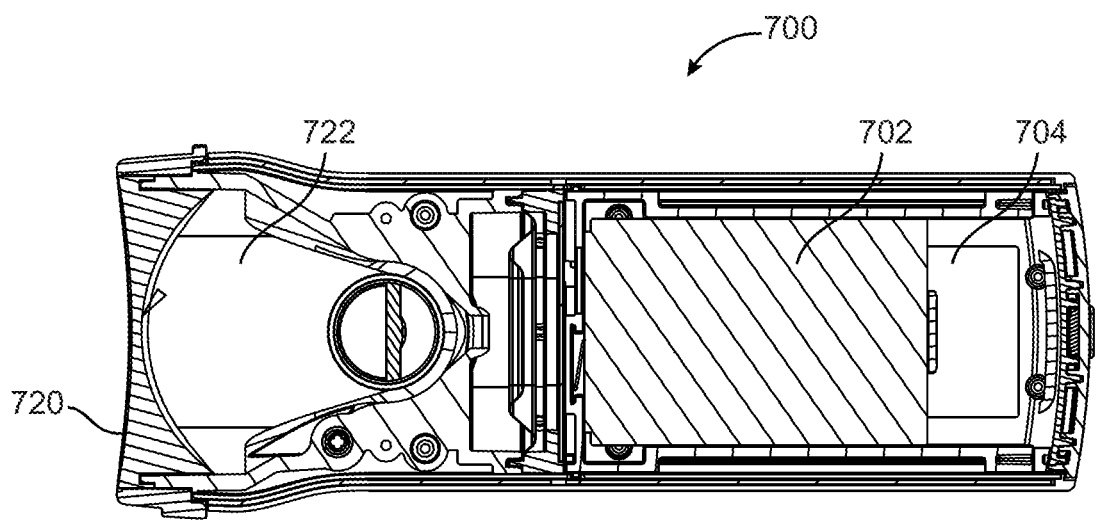
FIGS. 7A-B illustrate a horizontal and vertical cross section of an ultrasound probe according to an embodiment.
Figure 7B:
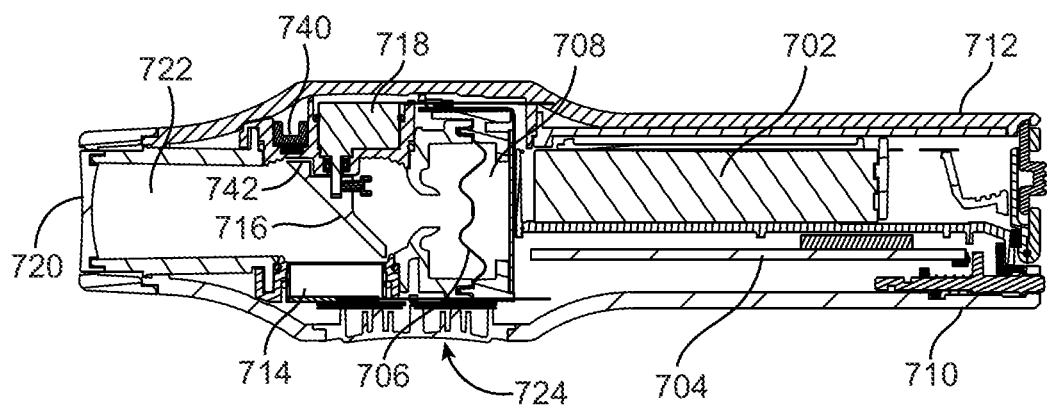

Various details of some embodiments are now shown in a pair of cross section views, one along the horizontal plane (FIG. 7A) and one along the vertical plane (FIG. 7B). A hand held probe 700 has a battery pack 702 contained in an electrical chamber. There is a PCB 704 in the electrical chamber and the battery 702 and PCB 704 are in electrical communication with each other. A fluid tight chamber 722 serves as the acoustic chamber of the probe and contains a transducer 714, rotating mirror 716 and motor 718 for driving the mirror. The acoustic chamber has a diaphragm 706 used to separate a fluid filled region 722 and a gas filled region 708. The acoustic chamber has a lens 720 at the front of the probe 700, and one or more controls 724 on the top surface (the transducer 700 is shown up-side-down in the illustration). The mirror 716 may have a reflector 742 on the base of it facing a sensor 740, so each revolution of the mirror can be counted and the exact position of the mirror determine at least once per revolution. In some embodiments the mirror rotates in a single direction at a constant speed. In other embodiments the mirror may rotate at variable speeds. In still other embodiments the mirror may rotate in two directions at a uniform or variable speed. In yet another embodiment the mirror may rotate in a stuttered manner where it rotates an incremental amount, pauses, and then rotates another incremental amount. The incremental amounts may be a uniform amount or different amount.

Figure 8:
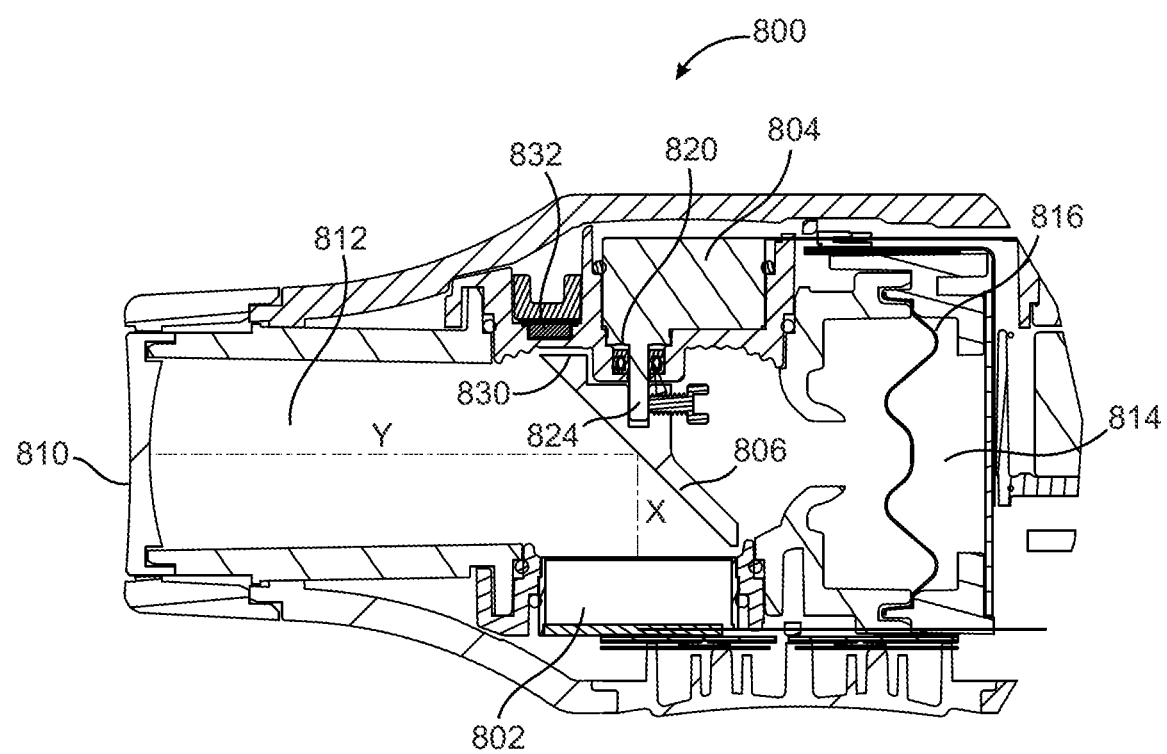
FIG. 8 illustrates a cross section of an acoustic chamber of the ultrasound probe according to an embodiment.

A closer view of the acoustic chamber 800 is shown in an embodiment (FIG. 8). The transducer 802 resides in a fixed location and projects ultrasound energy toward a mirror 806. The mirror rotates on an axis 824 driven by a motor 804. The motor may have an integrated gearbox. The axel may have a sealing O-ring 820 around it to prevent fluid flow into the compartment with the motor, however that is optional as the motor may operate equally well in a wet or dry environment. The membrane 816 is positioned to act as a pressure buffer for a fluid in the acoustic chamber 812. The membrane 816 can expand to fill a gas filled space 814. The membrane 816 helps keep the pressure of the coupling fluid generally constant, even if the fluid increases in volume due to temperature increase of the fluid during ultrasound scanning. It is generally beneficial to maintain the pressure of the fluid as constant so the mirror 806, lens 810 and transducer 802 do not experience changes in shape or coupling medium density due to pressure. The rotating mirror has one or more reflector(s) or other detectable feature 830 that can be read by a sensor 832. To address indexing of the motor position, the acoustic sensor can sense a reflector that is intentionally put in the path outside the active image area. A "power on" algorithm can be employed to find and register the index position to allow for proper image alignment. In an embodiment there can be an acquisition control block with a frame delay start from the index value. This allows the probe to accurately set the frame start once it determines the proper index mark for the motor and mirror. When the transducer emits acoustic energy toward the rotating mirror, the energy is reflected to the lens, which based on its curvature, refracts the acoustic beam generally straight out of the probe. Put another way, the acoustic lens rectifies the sector-scan created by the revolving mirror, effectively creating a rectilinear scan. In some embodiments, there may be a micro "stalactite" lining on the inner or outer part of the lens, to reduce the specular reflection from these surfaces. The structural lining can act the same way an anechoic chamber wall works, without absorption. The structure would have to be large enough to have an impact on direct specular reflection, without changing the refractions.

In an embodiment, the distance between the transducer 802 and the mirror 806 can be a first distance X. The distance between the mirror 806 and the lens 810 interior can be a second distance Y. X and Y are the primary axis of transmission for ultrasound energy. The ratio of the distance X:Y can be in some embodiments 1:3. In other embodiments the ratio of X:Y can be 1:4. In still other embodiments the ratio can be 1:5 or less. The ratio of X to Y need not be absolutely a whole number relationship. In discussing these ratios, the number of Y may vary by +/−0.5 either higher or lower than the whole number listed. So as a non-limiting example, the ratio could be 1:3.5-4.5 when referring to the ratio of 1:4. In various embodiments, the design of the probe promotes the increased Y distance relative to the X distance by having the transducer to mirror axis reduced to a short axis in the hand held probe. The distance from the mirror to the lens can be increased to reduce the curvature on the lens and improve resolution of the image produced during an ultrasound scan. In one aspect, the ratio may be 1:4 or less to reduce the curvature on the lens. Reducing curvature of the lens reduces the production cost on each individual lens, and decreases the distortion of the ultrasound signal as it passes through the lens. In another aspect, the ratio of the transducer to mirror and mirror to lens distance can also alter the shape of the lens, as the lens can be optimized to change the ultrasound signal shape. The adjustment on the ratio of X:Y can also cause an adjustment in the curvature of the lens. Parameters of the lens can be empirically determine or calculated using material data of the lens and data regarding the various aspect of the transducer, mirror and acoustic beam information (not shown).

Figure 9:
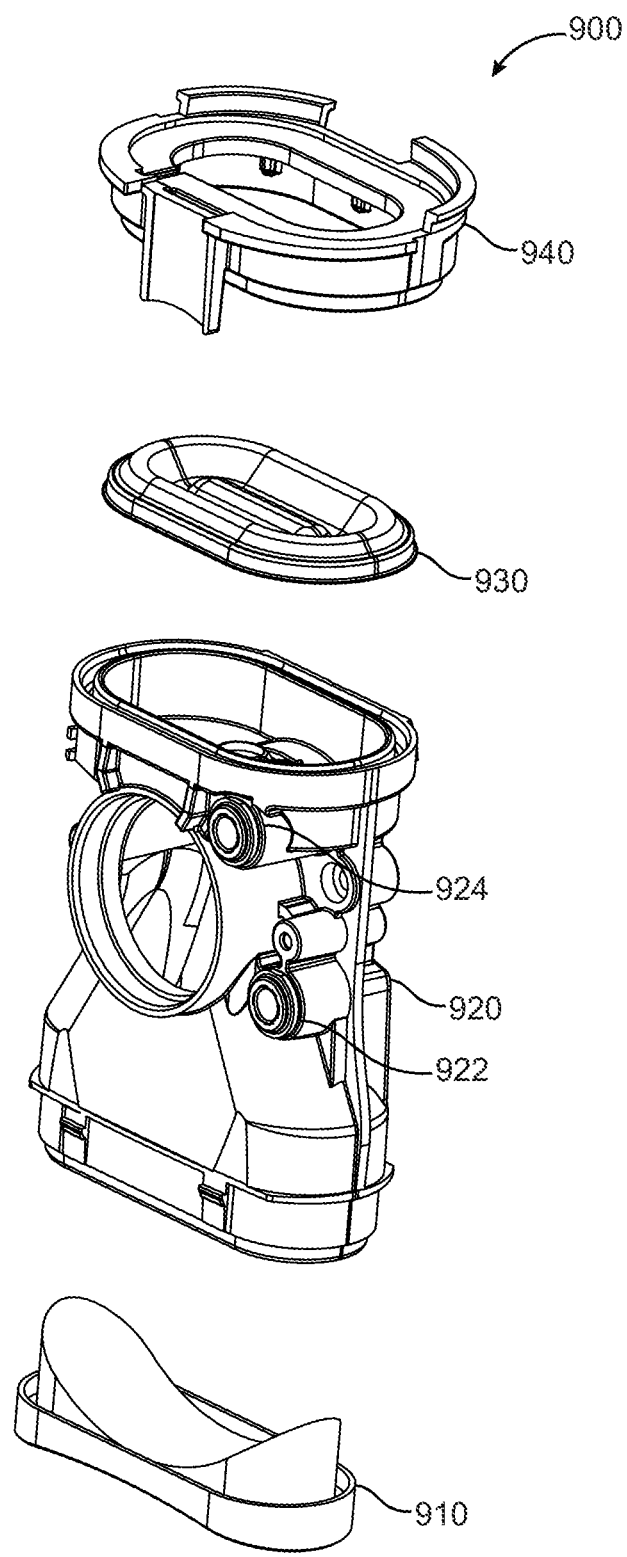
FIG. 9 illustrates a partial assembly view of the ultrasound chamber of the probe according to an embodiment.
Figure 10A:
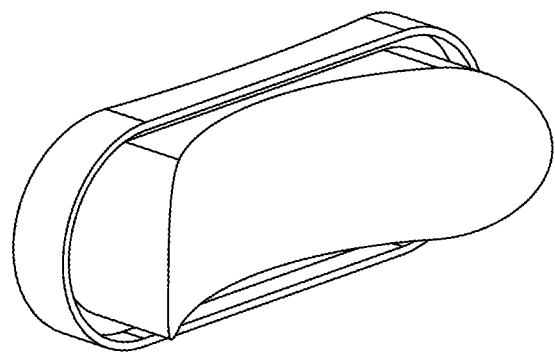
FIGS. 10A-B illustrate a front and back perspective image of an acoustic lens according to an embodiment.
Figure 10B:
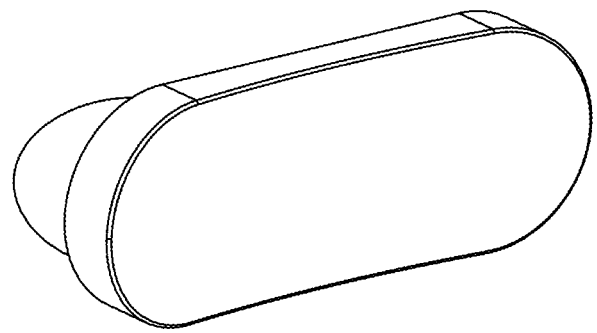
Figure 11A:
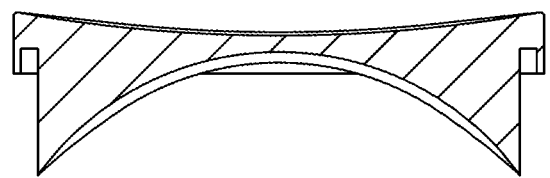
FIGS. 11A-C illustrate a cross section, front and top view of an acoustic lens according to an embodiment.
Figure 11B:
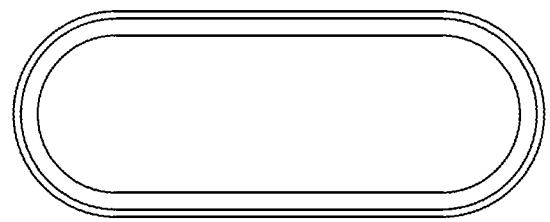
Figure 11C:
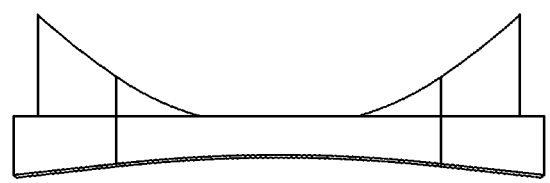

The acoustic chamber is now shown in a partial assembly view (FIG. 9). The acoustic chamber 900 has a lens 910 and a chamber housing 920. A membrane 930 provides the back end fluid seal to the chamber, while a non-flexible back wall 940 provides the end of the acoustic chamber and has gas in the space between the membrane 930 and the back wall 940. The components can be secured to each other using epoxy or other bonding agent. A fluid fill port 922 allows fluid to enter the acoustic chamber. An exhaust port 924 can be used to let air escape from the acoustic chamber as it is being filled with a coupling fluid. The exhaust port is slightly elevated when the probe is resting on a flat surface, allowing air to escape above the fill port and permit the complete evacuation of air from the chamber. A bubble trap resides near the membrane to trap any gas bubbles that may form once the acoustic chamber is sealed.

The lens is now shown (FIGS. 10A-B, FIGS. 11A-C). The lens can be made from a solid piece of acoustically transparent material, such as a cross linked polystyrene. In one non-limiting example, the lens may be made of Polystyrene CAS #9003-53-6. In an embodiment, the lens has a 27 mm inside spherical radius and a 134.7 mm spherical outside radius. The combination of material and shape provides a beam shaping to the reflected ultrasound energy so that the energy emitted goes out in substantially parallel paths. Other materials and spherical radii may be selected for different beam forming characteristics. In some embodiments, the inside curvature of the lens can be reduced (the interior curvature of the lens can be "flattened") if the distance between the lens and the mirror is increased. Reducing the curvature of the lens (flattening) can provide increased resolution of the image.

In another embodiment, there may be an anechoic surface on a portion of the transducer chamber. As used herein, the term "anechoic" refers to designs or materials that reduce the reflection of ultrasound energy (or sound energy) to the transducer or transducer source S. The term anechoic is not meant to indicate the ultrasound chamber is an anechoic chamber where no sound can be heard. The term is mean to describe areas of the chamber that reduce ultrasound energy reflection so the transducer receives ("hears") less ultrasound from unwanted reflections. The anechoic surfaces and/or materials are not meant to interfere with the reflected ultrasound signals that are used for creating an ultrasound image.

The anechoic surface may be a liner material added to the interior of the transducer chamber, or it may be integrated into the chamber when the chamber is formed.

Figure 20A:
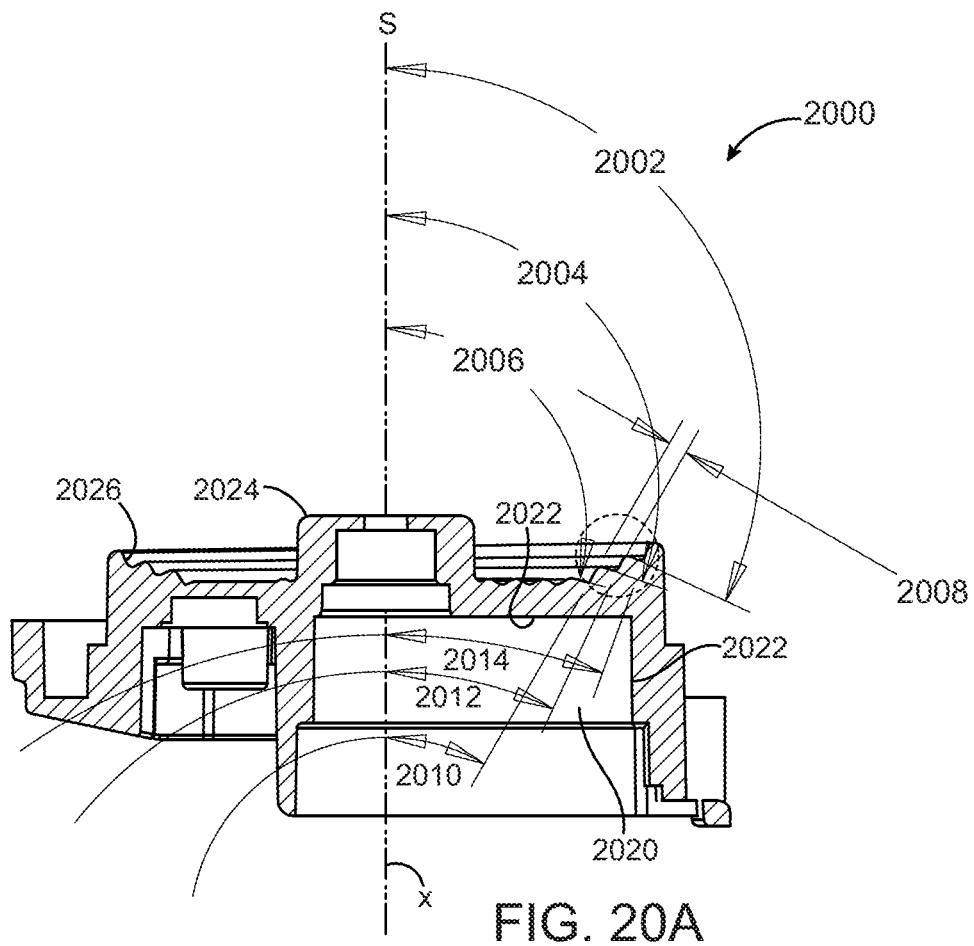
FIGS. 20A-20B illustrate an anechoic design around the mirror mount according to an embodiment.
Figure 20B:
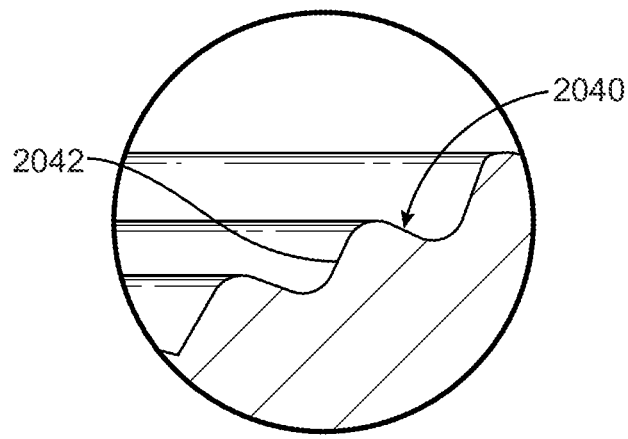

In an embodiment, the rotating mirror may sit in over a motor housing 2022 containing a motor assembly 2020 (FIG. 20A-B). The mirror platform 2024 can have a recessed base 2026. The recessed base 2026 allows the mirror to extend below the top of the mirror platform 2024. The mirror can be mounted on an axis in line with axis of rotation x. The recessed base 2026 may have a stepped region indicated by one or more step surfaces designated by their angle off the axis of rotation x. Borrowing nomenclature from architecture, the steps have two parts: the rise (the surface area between the top surfaces of successive steps) and the tread (the top of a step where one would put their feet). In an ordinary stair case, the tread is the horizontal landing, and the rise is the vertical plane between each tread. Obviously the steps described herein are not intended to be walked on, the terms are merely borrowed for discussion purposes. Here each rise and tread corresponds to a different angle off the axis of rotation x. The axis of rotation x is intended here to be the same axis that would be the center of the ultrasound transducer. If however the transducer were off set from the axis of rotation of the mirror, the axis defining the center of the ultrasound transmission beam would be based on the transducer, not the rotating mirror.

In an embodiment, the axis of rotation x corresponds to the central axis of ultrasound energy. The steps form rings around the recessed base 2026. The angle of each rise and each tread of each step may be different, so that each rise and tread reflects ultrasound energy at a different angle. In one non-limiting example, the step surfaces 2002, 2004, 2006 could be 115° 105° and 110° degrees respectively from the axis of rotation x. The rise angles 2014, 2012, 2010 might be 90° less than each tread, or 25°, 15° and 20° degrees of the axis of rotation x (Note—Figure and angles are not to scale). Note also the point where the rise 2042 and tread 2040 meet may be rounded instead of at a perpendicular angle (FIG. 20B). Each step may form a circular ring around the axis of rotation x, thus each angle for the rise and tread can be thought of as carving out a circular ring when the ray matching the angle is rotated around the axis x.

In some embodiments the steps need not be continuous, but could be fragmented or interrupted for alternative angles of rises and treads, or interrupted with other anechoic features to reduce reflection back on the transducer. In one aspect, the anechoic structure may have a break in it to increase reflection to the transducer for signal evaluation purposes. In still other embodiments the angles between the tread and rise could be more or less than 90°, with each step having a different angle between rise and tread, or all steps have the same angle between rise and tread and being an angle to help reduce ultrasound reflection back at the transducer. The junction of rise and tread may be sharp, rounded, faceted, roughened, etc. In some embodiments there may be three angled steps. In other embodiments there may be one, or any number desired. The two surfaces of each step provide an anechoic surface to reflect ultrasound energy away from the transducer. The intent being to reduce unwanted signal to the receive device(s). Ultrasound energy can be emitted down toward the mirror platform 2024 and recessed base 2026, generally along the center axis x. The mirror (not shown in FIG. 20 for clarity) rotates as the ultrasound energy is sent, and cuts through the cone of ultrasound waves to reflect ultrasound energy toward the lens (also not shown in FIG. 20). The imaging is done by reflected ultrasound received back through the lens and reflected on the mirror back toward the transducer source S. The anechoic surface helps reduce the reflected ultrasound from the initial pulse by scattering that ultrasound energy not directed by the mirror, into the chamber, so the transducer receives less primary reflection from each ultrasound pulse. Ultrasound energy that may be wider than the mirror can strike the recessed base 2026. To prevent that energy from reflecting immediately back at the transducer, the stepped surface acts like an anechoic surface and can deflect the ultrasound energy away from the transducer source. This can substantially reduce the amount of energy reflected back at the transducer so there is less signal on the receive side that has to be filtered out or compensated for.

Figure 21:
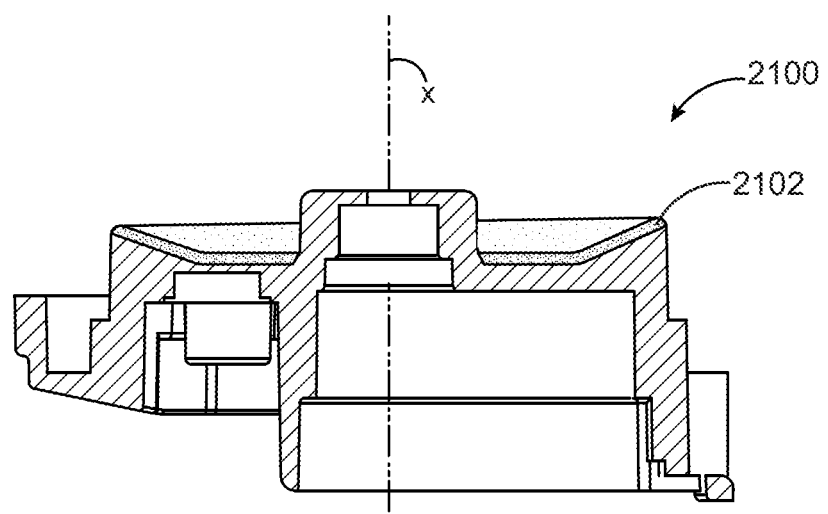
FIG. 21 illustrates an alternative anechoic design around the mirror mount according to an embodiment.

In some embodiments, the step feature for directional reflection of ultrasound energy may be replaced with an anechoic material that can absorb ultrasound energy and dampen any acoustic return off the surface (FIG. 21). In an embodiment, the transducer chamber 2100 may have an anechoic material like foam or rubber material 2102 having numerous pockets that help dampen ultrasound energy. In another aspect, the anechoic material or steps may be placed at various places within the ultrasound chamber to help reduce the intensity of reflected ultrasound energy. In another aspect, the ultrasound chamber may be completely coated with an anechoic material. In still another aspect, the interior surfaces of the transducer chamber may be molded or manufactured with a roughened surface to help disperse ultrasound energy that impacts it.

In some other embodiments, the anechoic surface can be any material or texture that can reflect or absorb signal reducing the energy that may get back to the transducer source S. This mechanical ability to decrease unwanted receive signals may be used to increase the "listen" window of the receive circuit, and/or reduce the noise the receive circuit has to filter when processing return signal from the patient. The anechoic features may also improve resolution.

Electronically, the receive circuit of the probe can be programmed to ignore return signals below a certain threshold. Alternatively the receive circuit can evaluate these signals as part of a diagnostic feature to evaluate the health or quality of the acoustic chamber, while still filtering out these signals when image processing is performed.

Figure 12:
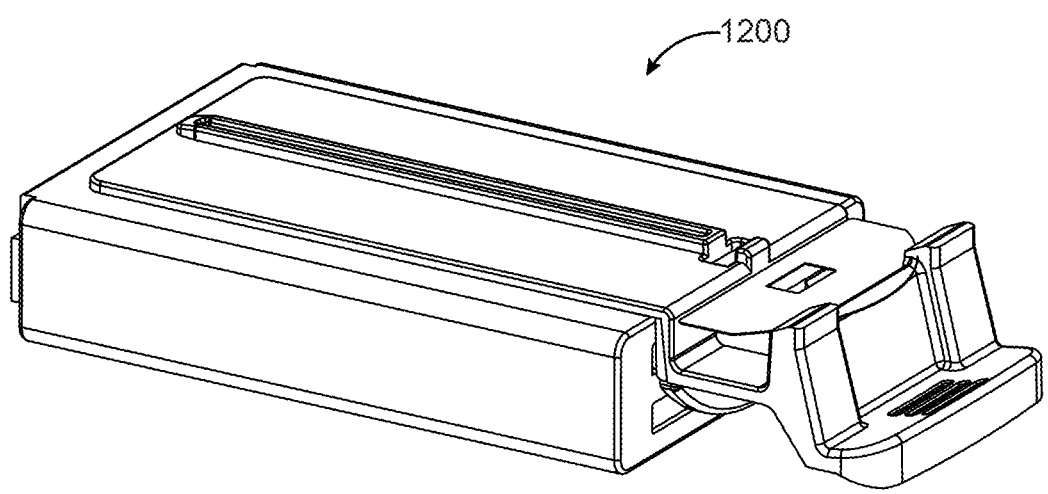
FIG. 12 illustrates a battery pack according to an embodiment.
Figure 13:
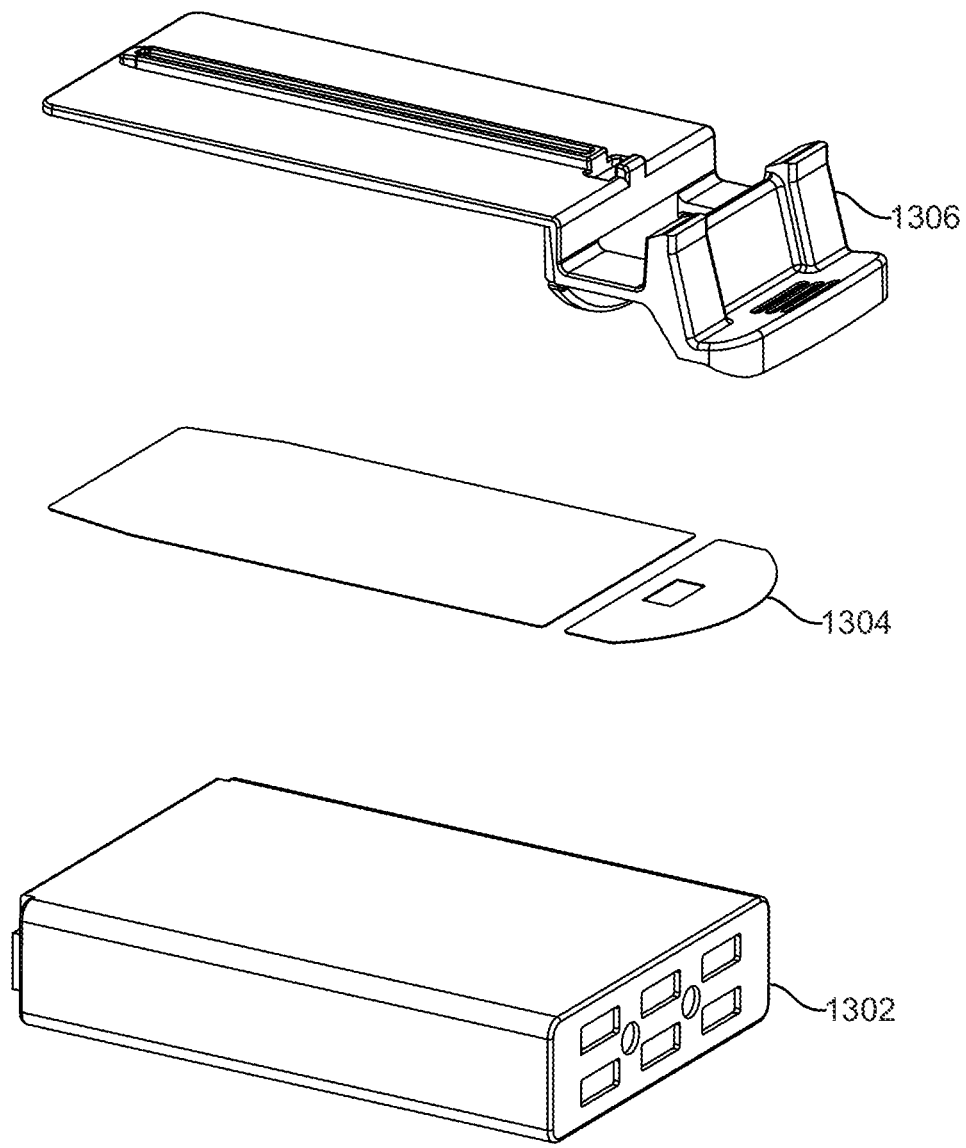
FIG. 13 provides a partial assembly view of a battery pack according to an embodiment.

An assembled battery pack 1200 is shown (FIG. 12) with a release liner and a battery bracket. The battery 1302 has a liner 1304 between the battery and a bracket 1306 (FIG. 13). The bracket 1306 ensures proper alignment of the battery when it is inserted into the probe, and has a grip for easy removal and insertion of the assembled battery pack into and out of the probe.

The probe described herein is generally a small, handheld and battery operated ultrasound transducer, acquisition and signal processing device to be used in conjunction with an external computer device. The external computer device may be a computer, laptop computer, tablet computer, personal data assistant (PDA), mobile phone (e.g. iPhone, Android, Blackberry or Windows), or other mobile computing device. Collectively any external computing device or suitable electronic device, used with the probe is referred to herein as a tablet. The probe may have a compact footprint and use an annular array that is reflected off a rotating mirror. This design can help reduce complexity and cost of the overall design.

The probe may provide the majority of the ultrasound signal path for the system including at least one of: a transducer, a motor, a mirror, an analog RX, TX, A/D conversion, RX and TX beamforming, and signal processing and detection to generate a 2D ultrasound image. A tablet can perform scan conversion and a speckle reduction algorithm and provides basic controls and the display for the image. The probe interfaces to the tablet through a WiFi interface. Alternatively, the speckle reduction algorithm may reside in the FPGA (on the probe electronics package) to reduce loading and allow other functions on the tablet.

In some embodiments, the transducer may be an 8 ring annular array transducer. The transducer can be fixed with the face of the transducer in a liquid filled chamber facing the mirror. The back side of the transducer may be outside the acoustic chamber, either in the wall between the two chambers, or with the back side in the electronics chamber. The transducer can have a flex connector coming off it to connect to the main board. In some embodiments, the transducer may be any single mechanically focused transducer having up to 8 elements. In other embodiments, the transducer may be a linear array, phased array, convex array, 2D array, mechanically scanned linear array, mechanically scanned convex array, or other form of transducer. The description herein provides details for an 8 element annular array, however any other transducer may be supported by scaling the necessary power and size as needed. The mirror, inside the acoustic chamber, can be rotated by a motor to translate the beam across in the azimuth direction. In some embodiments, the motor resides in the acoustic chamber, set in the acoustic chamber and has a motor shaft to the mirror. In some embodiments the motor may sit in a dedicated compartment that may be open to fluid, or sealed from fluid contact. In some aspects where the motor resides in a dedicated compartment and is sealed off from the fluid in the acoustic chamber, the motor shaft may be sealed by a quad ring type interface.

Figure 14:
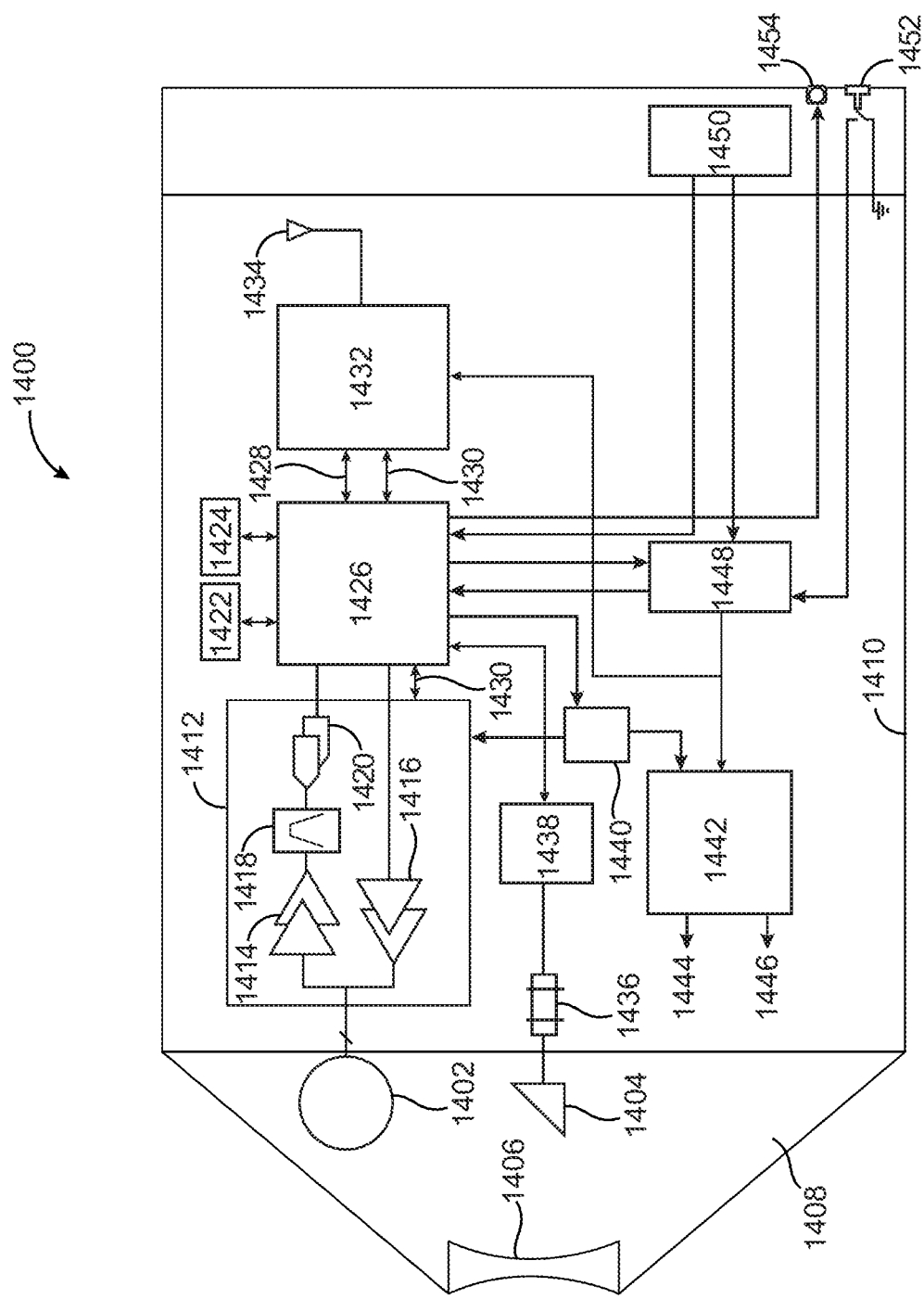
FIG. 14 illustrates a block diagram schematic of the ultrasound probe according to an embodiment.

The probe has an electronics package that provide transmit and receive functions for the transducer, communication to the tablet, and user controls for the operation of the probe. In an embodiment, the electronics package can be a circuit board with various electronic components on it. In some embodiments the circuit board may be removable or replaceable. In an embodiment, an overall schematic of the probe 1400 is provided (FIG. 14). The probe can have an annular array 1402 in an acoustic chamber 1408. The acoustic chamber 1408 may be filled with an ultrasound transmission fluid, such as water or oil. The acoustic chamber has a mirror 1404 mounted to a motor 1436 on a rotating shaft. While the motor 1436 is shown as part of the circuit board, it may physically be in either the acoustic chamber or the electronics chamber or in between. An acoustic lens 1406 provides beam shaping of the ultrasound energy as it exits the probe. The probe electronics may be on a single PCB (printed circuit board) 1410 can have a transceiver 1412 having both receive 1414 and transmit 1416 lines, with a dynamic weight line 1418 and analog to digital converter 1420. Transmit and receive data are generated in an FPGA (Field Programmable Gate Array) 1426 in electronic communication with a first memory 1422 and a second memory 1424. The memory units may be RAM (random access memory) or flash memory chips or removable units (such as flash drives). The FPGA is in electronic communication with a WiFi controller 1432 and a RF (radio frequency) antenna 1434, which can receive and transmit information to a tablet. The WiFi unit may provide control 1428 and serial peripheral interface 1430. In some embodiments, the WiFi controller may be integrated into the FPGA. A battery 1450 provides power to the probe and its components. The battery power can feed the FPGA directly, and go through an on/off switch 1448, which provides activated power to various power supplies 1442 and the FPGA and WiFi controller. The FPGA has a serial peripheral interface digital to analog converter 1440, with HV set point to the power supplies 1442. The FPGA also drives the motor controller 1438, and a serial peripheral interface connection 1430. The power supplies energy to a +/− variable HV line 1444 and an adjustment line 1446. The probe may also have an indicator light 1454 and a momentary switch 1452.

In an embodiment, the electronics package provides ultrasound transmit (TX), receive (RX) and processing functions for basic 2D imaging. The package has an 8 channel transmit and receive beamformer and provides delay accuracies of at about 10 ns (nanoseconds) on TX and RX. There can be dynamic receive delay to continuously keep the receive beam in focus. There is dynamic receive weight capability to smoothly bring in channels to the beamforming process, with RX/TX frequency range from 2.0 MHz to 12 MHz with programmable bandpass characteristics. The battery and power supplies can provide up to 2 A (amps) and programmable output voltages up to +/−90V sufficient for a variety of transducers. There can also be a flexible waveform control to support various transducers and additional modalities (e.g. 3D, 4D, Doppler, etc). The electronics package can provide digital signal processing support including quadrature bandpass filtering (QBP), detection and compression to output detected grayscale line data, programmable QBP to tailor the image based on desired characteristics and transducer response, and programmable compression curve to optimize the presentation of the image. There can also be a motor closed loop constant speed controller embedded in the FPGA to give precise angular velocity. In some embodiments the WiFi connectivity to the tablet provides an embedded microcontroller in the FPGA to manage the WiFi communications and WiFi chip, and the embedded microcontroller also sets up and enables the acquisition subsystem. The electronics package can also have a transmit voltage and current monitoring system with hardware limits to ensure safe and proper operation.

Figure 15:
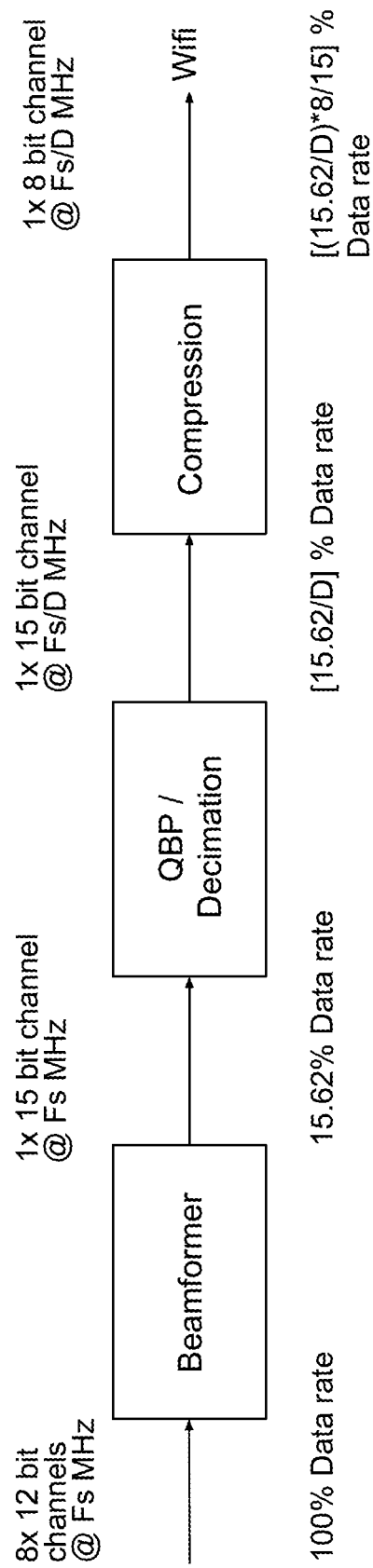
FIG. 15 illustrates a process for reducing image data for wireless transmission according to an embodiment.

In some embodiments, the probe may pre-process image data to reduce the wireless bandwidth of data transfer to a tablet (FIG. 15). In an embodiment of a probe using an 8 element annular array, the image data on the receive side may be 8×12 bit channels @50 MHz (the Sample Frequency or Fs). This represents 100% of the receive image data. The receive image data can be processed by the beamformer and reduced to a single 15 bit channel of the same frequency (50 MHz). This step represents a reduction in the data rate to about 15.62% of the 100% original data stream. A quadrature band pass/decimation operation can further reduce the data to about 15.62/D]% data rate (D being the variable based on the decimation value, and still using a single 15 bit channel at the sample frequency/D MHz. The image data can then be compressed using a known compression algorithm to produce a single 8 bit channel at the sample frequency/D MHz, and reducing the data rate even further to [(15.62/D)×8/15]% Data rate. The post compression data may be transmitted via WiFi and use between 1 to 15% of the original bandwidth of signal.

In some embodiments, each data image may further be tagged with an identifier, either as part of the reduced data stream, or as a label appended to the post compression data stream, that identifies the image set by one or more parameters. These parameters may be information such as various setting changes on the probe (like depth, power or frequency), or variations on the kind of scan performed on the patient. The tag bits can be used on the tablet side to identify the data image in a set of predefined "buckets" so the image data can be properly converted into accurate and useful display imagery for a user. These buckets might be parameters like 2D scan, 3D scan, 4D scan, Doppler, etc.

Figure 16:
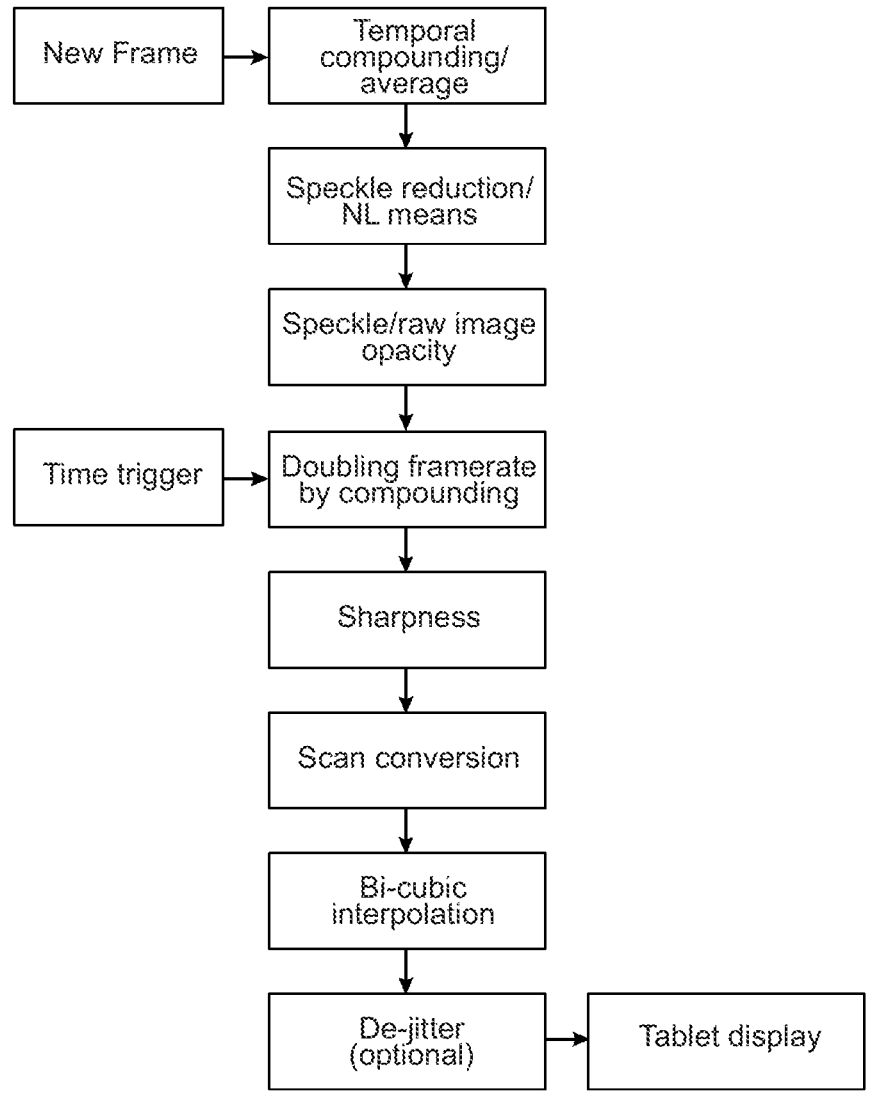
FIG. 16 illustrates a process for upscaling frame rate for image presentation of a video image according to an embodiment.

In some embodiments, a tablet or laptop can be programmed to properly display images from the probe. In an embodiment, there is a method for receiving a compressed ultrasound image from a probe, and converting it into a readable image without significantly increasing image latency (FIG. 16). Each new image is received in the tablet and queued for processing. The image may be raw data packets with no controller information. The data image is processed using a temporal compounding and averaging step. This provides noise reduction and averaging of two frames together and reduces the noise in each frame. It scales the image pixel conversion from 8 bits to 32 bits. Next the image may go through speckle reduction/NL (non-local) means, which identifies tissue and further reduces noise. A speckle/raw data opacity process can combine the images analyzed, and provides a method of presenting the image to the user. The image then goes through a process for doubling the framerate by compounding images. Here an algorithm can generate average data from the two previous processes to make an intermediate frame to artificially enhance the frame rate (which provides better visual quality to the user). The image can then be treated for sharpness, where average speckle enhances images and sharpens edges (images of tissue become better defined). The process then uses a scan conversion, bi-cubic interpolation and optional de-jitter step before displaying the image on a screen. The scan conversion and bi-cubic interpolation can take the received image data and convert it to the appropriate dimensions for the display device, enlarge or scale the image as needed, and otherwise insure the data is converted to the proper image format for the type of display device. De-jitter is an optional step that can compensate for image motion from frame to frame caused by the mechanical motion of the mirror and motor in the probe. This image smoothing is referred to as "de-jitter."

In some embodiments, the probe software and firmware can be upgraded over time without the need for the probe to be returned to the factory, or for a service visit by a factory representative. Each probe may carry specific software for optimization of the probe to a particular scan type. Alternatively the probe may have a library for storing different software modules to enable the probe to handle a variety of scan modes on demand. The software of the probe may be upgraded periodically by synchronizing (synch) with the display device used to view scanned images.

In an embodiment, the display device may download software for the displaying of scanned ultrasound images from the probe. The software for the display device includes the necessary code and libraries to control the probe wirelessly as needed, manipulate the image data, and perform data manipulation. In addition to the software for the visualization of probe scans, the display device may also download an attached module to the display software module. The attached module carries the complete software image of the probe, and the probe can be fully updated from the display device when the two are synched together. The attached module downloaded to the display device may contain all necessary libraries, and firmware updates for FPGA, WiFi or other hardware elements of the probe as needed. The hardware elements may include electronic components in the electronics package, or electrically driven components in the transducer compartment, like the motor, sensor, or transducer (if an electronically controlled transducer is used). Any element in the probe that uses any form of software, firmware, or the like may be updated using this method.

In an embodiment, when the probe is turned on and paired with the display device, the probe can access the additional module on the display device (or the display device can push the additional module available to the probe) so the probe may run through a series of checks to verify the probe has the necessary software version loaded. This includes cycling through the hardware chips on the probe to ensure each chip has the proper firmware or software needed to perform as intended. If a user has a preference for a type of ultrasound scan, the user can purchase or download the appropriate software to have the best visualization of the scanned images, and the added module that optimizes the probe for that particular kind of ultrasound scan. The user can then pair the probe to the display device, and the probe can retrieve the software and firmware needed from the users display device. This ensures each probe is customized for each user, and the image scan is optimized both in the probe for scanning, and in the display device for image review. When the probe is being updated, the individual chips or circuits of the probe may be updated serially or in parallel, or a combination of serially and parallel.

Some examples of the methods of use are now provided.

EXAMPLE I

This is a non-limiting example of how image enhancement on a tablet device might be performed. A new image is received by the tablet and a program does noise reduction on the image by temporal compounding and averaging, using two adjacent frames. This reduces the noise in each source frame. This is the first step of image post processing. It averages coming frame and the previous frame pixel by pixel. This reduces random noise and highlights stable areas like tissue.

Next is Speckle reduction. This step is noise removal algorithm. It has several levels that can be defined by the user. Speckle reduction uses standard algorithm. Then the tablet can perform Speckle and Raw Image Opacity, which mixes image filtered by speckle algorithm and raw image. A Double frame rate step creates an intermediate frame by averaging consequent frames. By inserting average frame into image stream, visible frame rate is doubled. The next step is Sharpness, which applies a standard Gaussian unsharp mask. It is a standard method to highlight image sharpness. The sharpening process works by utilizing a slightly blurred version of the original image. This is then subtracted away from the original to detect the presence of edges, creating the unsharp mask (effectively a high-pass filter). Contrast is then selectively increased along these edges using this mask—leaving behind a sharper final image.

The equation is:

UNSHARP_MASK=ORIGINAL_IMAGE-
   BLURRED_COPY
   SHARPENED_IMAGE=ORIGINAL_IMAGE+
   (strength*UNSHARP_MASK)

Next is the scan conversion phase, which fixes the image sector geometry that is due to distortion of the lens and oil. Bicubic Interpolation does standard bicubic algorithm per pixel.

EXAMPLE II

In an embodiment, there can be a method for synchronizing wireless ultrasound image data through a processing pipeline. The wireless ultrasound system may have two components, an ultrasound probe that creates ultrasound image by sending and receiving ultrasound signal to the target under investigation, and a user interface unit that may control the probe and that displays streaming video data that is the ultrasound image.

In an aspect, the user interface unit can activate the scanner, and provide image acquisition related parameters to the scanner. Then the scanner may send ultrasound image frames to the user interface unit through a wireless connection. The user interface unit may create near real time video streaming type of ultrasound images based on separate image frames send by the scanner. The scanner can send 10-30 image frames per second. The scanner may create image frames based on ultrasound acquisition and it pre-process image frames to reduce the use of wireless bandwidth, this may also help to improve image quality. The user interface unit can have post processing function for image frames to create video type of stream for the user and to improve image quality. In some embodiments the user interface unit may be a tablet device, cell phone, PDA, laptop computer, smart watch, wearable electronic device, or other generic or specially designed computer device.

In some embodiments, the user may want to modify image acquisition parameters depending on the medical use case. The user interface face unit can send modified parameters through the wireless link and the scanner can modify the acquisition or pre-processing parameters. After modifying the parameters, the content of the ultrasound image frame may change illustrating the modified parameters. In some embodiments modified image acquisition and post-processing parameters can be applied to each image frame. The user interface unit can detect accurately when modified images are available, and it can adjust image post processing algorithms. The user interface unit can indicate to the user that the modifications are now visible on the screen. Also the scanner can include all image frame parameters that are relevant for the image frame. For example the scanner can include gyro information that can be used for image post processing. Some example parameters included in an ultrasound image frame are frequency, gain, dynamic range, timestamp, gyro parameters and temperature. Additional parameters may be identified and included as desired.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on one or more computer storage medium for execution by, or to control the operation of, data processing apparatus, such as a processing circuit. A processing circuit such as CPU 160 or 142 may comprise any digital and/or analog circuit components configured to perform the functions described herein, such as a microprocessor, microcontroller, application-specific integrated circuit, programmable logic, etc. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

EXAMPLE III—Software/Firmware Update Process

In this non-limiting example embodiment, the updates to the memory of the probe occur when a check against software versions shows an upgrade may be needed. Not all instances of synching the probe to the display device will require an upgrade. Described in this example is a fail-safe upgrade sequence. This upgrade may be for a complete update of the probe, or a partial update.

Figure 17:
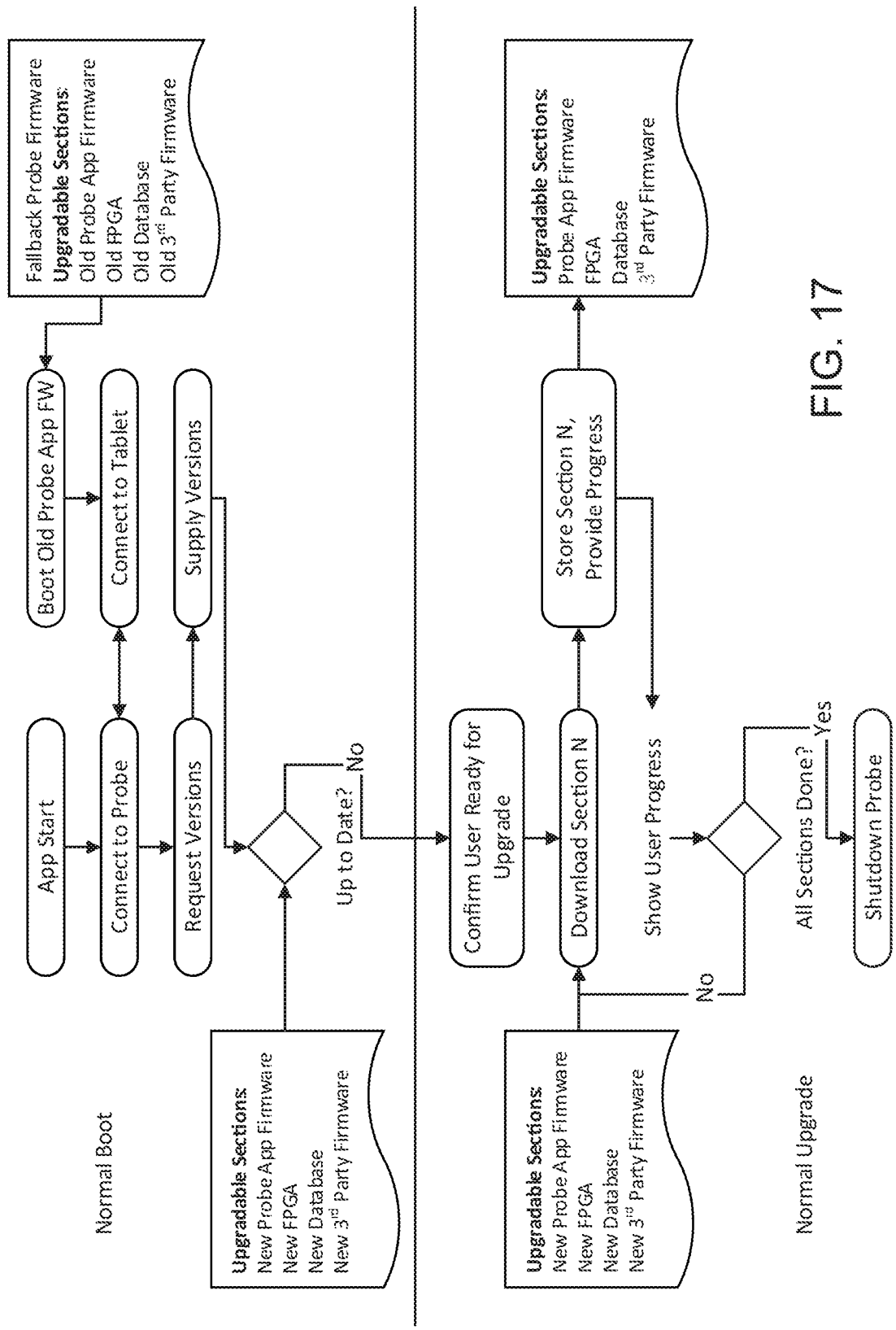
FIG. 17 illustrates a flow chart of a normal boot and normal upgrade path for the ultrasound probe according to an embodiment.

Initially the probe may verify data integrity while booting. The FPGA can support a dual boot mode and may boot from its primary image if the primary image is valid (FIG. 17). Alternatively the probe may boot from the backup image if the primary image is invalid. In some embodiments, the backup image is not changed and used as a default original image. Alternatively the backup image may be designated as some verified safe past version of the image, but not as recent than the image currently being updated. The backup image can be used to complete an update if the primary image is corrupted. Upgrade of the various components may be done serially (one after another) or in parallel (all at once) or any combination of the two. Examples of chip updates are illustrated using the WiFi chip as an example. The process of updating individual chips is about the same for each and may be done in no particular order.

Figure 18:
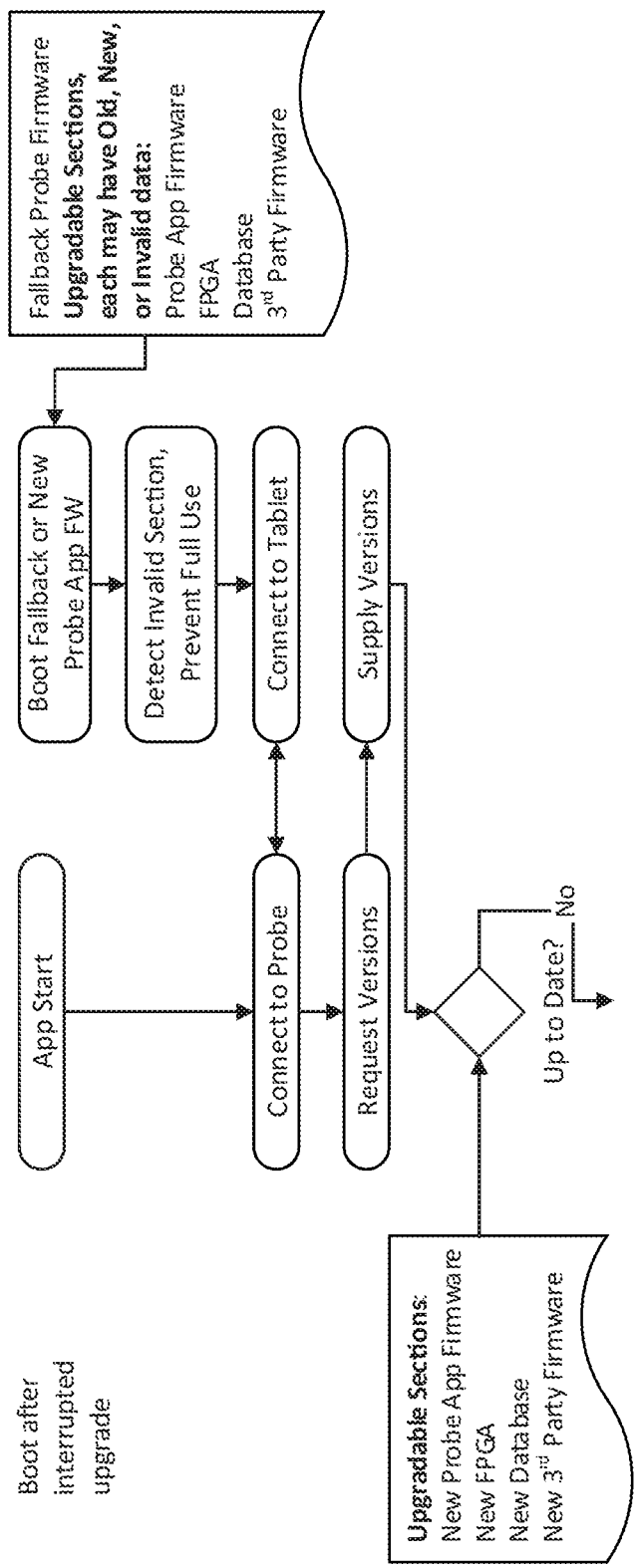
FIG. 18 illustrates a flow chart of a boot after an interrupted upgrade according to an embodiment.

A WiFi chip can boot from its embedded firmware if it is valid (or back up if the primary is invalid). The probe SW will check if the WiFi chip failed to boot, or if the firmware image (service pack and signature) in flash is both newer than what is in the WiFi chip and known to be valid based on the Cyclical Redundancy Code (CRC) stored in flash. If that is the case, the scanner SW will load the newer, valid, firmware image into the WiFi chip and reboot that peripheral. The following sequence should ensure that either the firmware image in the chip, or the firmware image in flash is always valid (FIG. 18). The scanner SW will check the validity of the probe data in flash using the CRC stored with the data. It will also check the version of the probe data to ensure it is at least as new as is needed by the current software. If the data is invalid or obsolete the software will go to its error state, but allow connection from the GUI SW and downloading of valid data.

If problems occur during the upgrade, the follow sequence should allow recovery from the issues and complete the upgrade. If both the probe software (SW) and the display device SW are restarted in the middle of an upgrade, the display device SW should detect the error state from the partial upgrade when it connects to the scanner. It should then confirm that it (the display device SW) has the upgrade data related to the partial upgrade the probe has received and it should complete the upgrade at that point. If the probe SW is restarted in the middle of an upgrade and connects to an older version of the display device SW that is not capable of completing the upgrade, it will remain in the error state until it is connected to the display device SW that started the upgrade.

In another example, the FPGA image is upgraded. The display device SW will download a new FPGA image to primary FPGA image in flash memory. The display device SW will wait until writing of the new image is 100% complete. Then it will shut down. The display device SW will tell the user to power (cycle power?) on the probe. The probe will detect that the primary FPGA image requires newer probe and/or WiFi data and go to an error state while it waits for the upgrade to complete. The new software is now running, so any custom processing that is needed to complete the upgrade can be performed at this stage. In particular, the new software may want to detect the old versions of WiFi firmware or probe data and consider them invalid to force the upgrade to complete if power is lost before they are upgraded (since they may still look valid from an integrity check).

WiFi firmware is upgraded. The display device SW can download new WiFi firmware and signature to flash memory on the probe. The display device SW can wait until writing of the new firmware is 100% complete. Validation of the download firmware may be performed during the boot in the final validity check.

Figure 19:
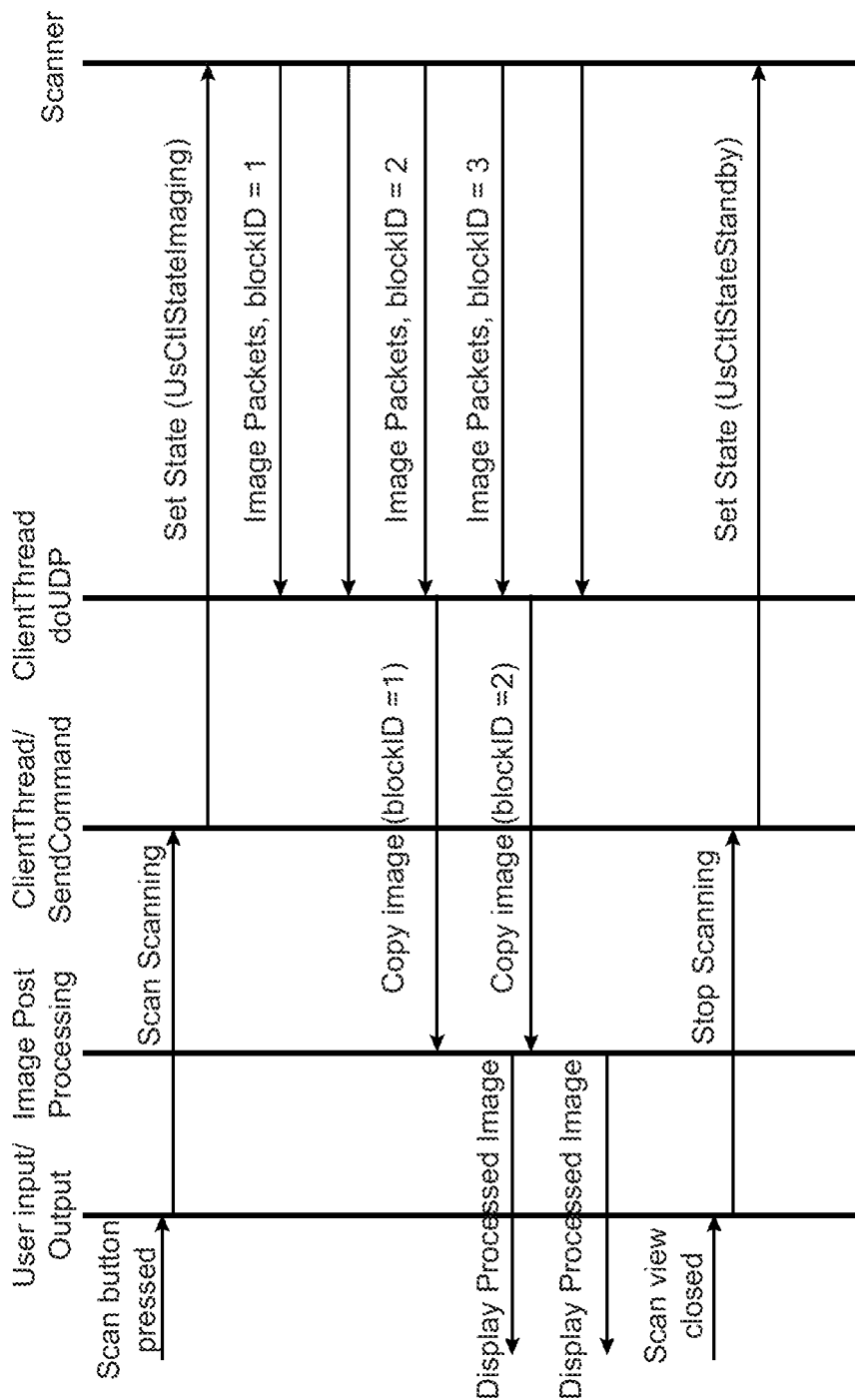
FIG. 19 illustrates a flow chart of data exchange between a display device and an ultrasound probe according to an embodiment.

Next the probe data is upgraded (FIG. 19). The display device SW can download new probe data including Cyclical Redundancy Code (CRC) to flash memory. The display device SW can wait until writing of the probe data is 100% complete. Validation of the download probe data can be performed during the boot in the final validity check.

Once all SW and FW is upgraded, the display device can perform a final validity check. The display device SW can issue command to restart the probe software (this may not reload the FPGA, just reset the processor). The display device SW can validate all software on boot as describe above. If the validation succeeds, the display device SW can see no error when it connects. If the validation fails, the display device SW may see an error indicating what is invalid when it connects. The display device SW should check that it has the upgrade data associated with the currently running version of software on the probe. The display device SW should continue the upgrade starting with the first invalid data detected.

EXAMPLE IV: Dynamic Nonvolatile Data

In this non-limiting example embodiment, dynamic nonvolatile data are any data which is dynamically updated by the probe. To ensure the stored data is not lost in the case of a power failure, two redundant copies are stored in flash memory. Each write of new data can be performed with the following sequence:

Each read of new data can be performed with the following sequence:
1. The validity of the primary section can be checked by reading that section and comparing the CRC of that section to the CRC stored with it.
2. If the validity check passes the data from the primary section can be used.
3. If the validity check fails, then the validity of the backup section can be checked by reading that section and comparing the CRC of that section to the CRC stored with it.
   a. If the validity check passes the data from the backup section can be used.
   b. If the validity check fails, an error may be created.

Additional example embodiments include the following:
1. A method comprising:
   receiving, by an ultrasound probe, software version data from a user computing device, wherein the user computing device comprises a display configured to display images from the ultrasound probe;
   determining, by the ultrasound probe, based upon comparison of data on the ultrasound probe with the software version data from the user computing device that an upgrade is available to the ultrasound probe;
   receiving, by the ultrasound probe, a software upgrade data into a memory module of the ultrasound probe, wherein the software upgrade data comprises data for upgrading at least one portion of the ultrasound probe; and
   upgrading, by the ultrasound probe, the at least one portion of the ultrasound probe from the software upgrade data.
2. The method of clause 1, further comprising establishing communication by the ultrasound probe with the user computing device for synchronizing the ultrasound probe and the user computing device before accessing

| | Procedure | Primary Contents | Backup Contents |
|---|---|---|---|
| 1. | Before any write of new data, the backup section can be checked for validity by reading that section and comparing the computed CRC to the CRC stored with it. | Old | Old |
| | a. If it is invalid the primary section including the CRC stored in it can be copied to the backup section and the validity of the backup section can be checked before proceeding. If it is still invalid, an error can be created and the writing can be aborted. | Old | Valid Old |
| 2. | If only part of the data is being updated, the previous data can be read (see sequence below) into RAM and the new data can be merged into that new full image. | Valid Old | Valid Old |
| 3. | A CRC can be computed for the new full image. This CRC may not include stored CRC data in the computed CRC. | Valid Old | Valid Old |
| 4. | The new full image and CRC can be written to the primary section of flash memory. | New | Valid Old |
| 5. | The validity of the primary section can be checked by reading that section and comparing the CRC of that section to the CRC stored with it. If the validity check fails, an error may be created and the backup section might not be affected. | Valid New | Valid Old |
| 6. | The new full image and CRC can be written to the backup section of flash memory. | Valid New | New |
| 7. | The validity of the backup section can be checked by reading that section and comparing the CRC of that section to the CRC stored with it. If the validity check fails, an error can be created. | Valid New | Valid New | an upgrade module of the user computing device for obtaining the software upgrade data.

3. The method of clause 1, wherein the at least one portion of the ultrasound probe is a component of the ultrasound probe comprising firmware.

4. The method of clause 1, further comprising:
cycling, by the ultrasound probe, through a plurality of hardware chips on the ultrasound probe to determine whether each of the plurality of hardware chips has a current version of software stored thereon, wherein cycling through the plurality of hardware chips comprises comparing data on the plurality of hardware chips with the software version data from the user computing device to determine if a software upgrade is available for any of the plurality of hardware chips.

5. The method of clause 1, wherein the software upgrade data comprises software that is optimized for a specific scan type performed by the ultrasound probe.

6. The method of clause 1, further comprising:
booting, by the ultrasound probe, the at least one portion of the ultrasound probe from a primary image or a backup image;
comparing, by the ultrasound probe, a computed cyclical redundancy code from the at least one portion of the ultrasound probe with a cyclical redundancy code of the software upgrade data;
determining, by the ultrasound probe, that software of the at least one portion of the ultrasound probe is outdated based upon the computed cyclical redundancy code being different from the cyclical redundancy code of the software upgrade data; and
updating, by the ultrasound probe, the software of the at least one portion by downloading the software upgrade data from the memory module into the at least one portion of the ultrasound probe.

7. The method of clause 6, wherein the ultrasound probe causes the at least one portion of the ultrasound probe to enter an error state upon determining that the software of the at least one portion of the ultrasound probe is outdated.

8. The method of clause 1, further comprising:
receiving, by the ultrasound probe, a rebooting command from the user computing device after receiving the software upgrade data;
rebooting, by the ultrasound probe, in response to the rebooting command;
determining, by the ultrasound probe, upon rebooting that a firmware of the ultrasound probe is outdated; and
updating, by the ultrasound probe, the firmware from the software upgrade data.

9. The method of clause 1, wherein the software upgrade data comprises upgraded software for a component of the ultrasound probe.

10. The method of clause 1, further comprising:
reading, by the ultrasound probe, a backup section of the at least one portion and verifying that data within the backup section is valid;
computing, by the ultrasound probe, a new cyclical redundancy code for the at least one portion from the software upgrade data;
writing, by the ultrasound probe, the software upgrade data into a primary section of the at least one portion; and
comparing, by the ultrasound probe, the new cyclical redundancy code with a cyclical redundancy code stored with the software upgrade data for verifying the validity of the software upgrade data in the primary section.

11. A method comprising,
receiving, by a user computing device, software upgrade data for upgrading software of an ultrasound probe, wherein the user computing device comprises a display configured to display images from the ultrasound probe;
establishing communication, by the user computing device, with the ultrasound probe;
receiving, by the user computing device, an indication from the ultrasound probe for upgrading the ultrasound probe;
downloading, by the user computing device, the software upgrade data onto the ultrasound probe;
receiving, by the user computing device, confirmation that the software upgrade data is successfully downloaded onto the ultrasound probe; and
issuing, by the user computing device, a rebooting command for causing a reboot of the ultrasound probe.

12. The method of clause 11, further comprising:
validating, by the user computing device, the software of the ultrasound probe upon rebooting; and
determining, by the user computing device, that the upgrade is not successfully completed upon receiving at least one indication of error from the ultrasound probe.

13. The method of clause 12, further comprising:
continuing upgrade, by the user computing device, of components of the ultrasound probe that caused the at least one indication of error.

14. The method of clause 11, further comprising:
validating, by the user computing device, the software of the ultrasound probe upon rebooting; and
determining, by the user computing device, that the upgrade is successfully completed upon receiving no indication of error from the ultrasound probe.

15. A system comprising:
an ultrasound probe comprising a probe memory module and probe processing unit; and
a user computing device configured to be operatively associated with the ultrasound probe comprising a display configured to display images obtained by the ultrasound probe, the user computing device further comprising a device memory module and a device processing unit, and
wherein the probe processing unit is configured to:
access an upgrade module on the device memory module of the user computing device;
determine based upon comparison of data on the ultrasound probe with software version data from the upgrade module that an upgrade is available to the ultrasound probe;
receive software upgrade data from the upgrade module into the probe memory module of the ultrasound probe, wherein the software upgrade data comprises data for upgrading at least one portion of the ultrasound probe; and
upgrade the at least one portion of the ultrasound probe from the software upgrade data.

16. The system of clause 15, wherein the device processing unit is configured to:
receive the upgrade module and store the upgrade module in the device memory module;

receive indication from the ultrasound probe to upgrade the ultrasound probe;

download the software upgrade data from the upgrade module onto the probe memory module;

receive confirmation that the software upgrade data is successfully downloaded onto the probe memory module; and issue a rebooting command to cause a reboot of the ultrasound probe.

17. The system of clause 15, wherein the probe processing unit and the device processing unit are configured to establish a synchronization between the ultrasound probe and the user computing device upon receiving an indication of pairing from the ultrasound probe.

18. The system of clause 15, wherein the user computing device is a tablet or laptop.

19. The system of clause 15, wherein the probe processing unit is further configured to pre-process image data obtained by the ultrasound probe and transmit the pre-processed image data to the user computing device, and wherein the device processing unit is further configured to process the pre-processed image data to obtain a final image.

20. The system of clause 15, wherein the software upgrade data comprises data for upgrading software of at least one component on the ultrasound probe.

21. A method of minimizing ultrasound image data, the method comprising:

performing a first bit channel reduction on a data set;

reducing a percent data rate on a data set; and altering a sample frequency (Fs MHz) based on a variable produced by a decimation reduction of a sample bit (Fs/D MHz);

wherein an image data set is reduced in bit volume by at least 80%.

22. A method of enhancing ultrasound image data, the method comprising:

receiving a first and a second reduced image data set;

creating an intermediate image data set by averaging the first and second image;

interleaving the first and second image data sets with the intermediate image data;

adjusting all image data sets for a display; and exporting the image data sets to the display.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices). Accordingly, the computer storage medium is both tangible and non-transitory.

The operations described in this specification can be implemented as operations performed by a data processing apparatus on data stored on one or more computer-readable storage devices or received from other sources. The term "data processing apparatus" or "computing device" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. In some cases, the actions recited herein can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." Further, unless otherwise noted, the use of the words "approximate," "about," "around," "substantially," etc., mean plus or minus ten percent.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A hand held ultrasound transducer probe comprising:
   a housing defining a first chamber and a second chamber within the housing, the first chamber comprising an electronics package and a power supply, and the second chamber being a liquid tight chamber comprising:
   an ultrasound transducer having a primary axis of transmission defining a first axis X, wherein the electronics package is configured to drive the ultrasound transducer;
   an acoustic mirror;
   a drive motor for moving the acoustic mirror;
   an acoustic lens aligned with the acoustic mirror;
   a flexible membrane to partition the second chamber into a first section and a second section; and
   an anechoic region comprising a plurality of annular steps each defining a plane oriented to reflect ultrasound energy outwardly away from the primary axis of transmission, the anechoic region positioned such that the plurality of annular steps are positioned outside of the primary axis of transmission;
   wherein the first section is adapted to contain an ultrasound transmission fluid and includes the ultrasound transducer, the acoustic mirror, the anechoic region, and the drive motor, and the second section contains a gas such that the flexible membrane may expand into the second section.

2. The hand held ultrasound transducer probe of claim 1, wherein a second axis of transmission Y is defined by the acoustic mirror and the acoustic lens.

3. The hand held ultrasound transducer probe of claim 2, wherein the ratio of the first axis X to the second axis of transmission Y is less than 1:3.

4. The hand held ultrasound transducer probe of claim 1, wherein the electronics package further comprises a wireless communication circuit, a transmit image buffer, and an adjustable network address.

5. The hand held ultrasound transducer probe of claim 1, wherein the second chamber further comprises:
   a sensor in a fixed position and lined up with the acoustic mirror so the sensor is within a circumference area defined by the acoustic mirror; and
   a reflector on the acoustic mirror and positioned to be detected by the sensor, such that as the acoustic mirror moves, the reflector is detected each time it passes over the sensor.

6. The hand held ultrasound transducer probe of claim 1, wherein the second chamber further comprises an anechoic feature.

7. The hand held ultrasound transducer probe of claim 1, wherein the each of the plurality of steps has a separate tread arc and rise angle.

8. The hand held ultrasound transducer probe of claim 6, wherein the anechoic feature is a lining material.

9. The hand held ultrasound transducer probe of claim 1, wherein the electronics package is configured to perform a decimation reduction of a sample bit to reduce data volume by 80%.

10. The hand held ultrasound transducer probe of claim 1, wherein the hand held ultrasound transducer probe weighs less than 250 g.

11. The hand held ultrasound transducer probe of claim 1, wherein the second chamber further comprises a fill port and an exhaust port.

* * * * *